United States Patent
Ban et al.

(10) Patent No.: US 12,178,879 B2
(45) Date of Patent: Dec. 31, 2024

(54) HEMIASTERLIN DERIVATIVE AND ANTIBODY-DRUG CONJUGATE THEREOF

(71) Applicant: Sumitomo Pharma Co., Ltd., Osaka (JP)

(72) Inventors: Hitoshi Ban, Osaka (JP); Atsushi Suwa, Osaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 815 days.

(21) Appl. No.: 17/429,427

(22) PCT Filed: Feb. 12, 2020

(86) PCT No.: PCT/JP2020/005291
§ 371 (c)(1),
(2) Date: Aug. 9, 2021

(87) PCT Pub. No.: WO2020/166592
PCT Pub. Date: Aug. 20, 2020

(65) Prior Publication Data
US 2022/0125941 A1 Apr. 28, 2022

(30) Foreign Application Priority Data
Feb. 13, 2019 (JP) .................................. 2019-023961

(51) Int. Cl.
A61K 45/06 (2006.01)
A61K 47/68 (2017.01)
C07K 16/28 (2006.01)
A61K 39/00 (2006.01)

(52) U.S. Cl.
CPC .......... *A61K 47/6803* (2017.08); *A61K 45/06* (2013.01); *C07K 16/2878* (2013.01); *A61K 2039/505* (2013.01)

(58) Field of Classification Search
CPC .............. A61K 47/6803; A61K 45/06; A61K 2039/505; C07K 16/2878
See application file for complete search history.

(56) References Cited

U.S. PATENT DOCUMENTS

| | | |
|---|---|---|
| 6,153,590 A | 11/2000 | Andersen et al. |
| 7,579,323 B1 | 8/2009 | Andersen et al. |
| 2004/0229819 A1 | 11/2004 | Kowalczyk et al. |
| 2009/0136526 A1 | 5/2009 | McDonagh et al. |
| 2011/0171125 A1 | 7/2011 | Elkins et al. |
| 2015/0366990 A1 | 12/2015 | Park et al. |
| 2017/0007714 A1 | 1/2017 | Kontermann et al. |
| 2017/0008945 A1 | 1/2017 | Madsen et al. |
| 2017/0335284 A1 | 11/2017 | Masuda et al. |
| 2022/0202948 A1* | 6/2022 | Suwa ............... A61K 47/6849 |

FOREIGN PATENT DOCUMENTS

| | | |
|---|---|---|
| JP | H11-505211 A | 5/1999 |
| JP | 2005-508877 A | 4/2005 |
| JP | 2005-530717 A | 10/2005 |
| JP | 2007-537136 A | 12/2007 |
| JP | 2011-500725 A | 1/2011 |
| JP | 2012-522513 A | 9/2012 |
| JP | 2016-504355 A | 2/2016 |
| JP | 2016-516063 A | 6/2016 |
| JP | 2017-502047 A | 1/2017 |
| JP | 2017-506234 A | 3/2017 |
| JP | 2017-508741 A | 3/2017 |
| WO | 96/033211 A1 | 10/1996 |
| WO | 03/006506 A2 | 1/2003 |
| WO | 03/082268 A2 | 10/2003 |
| WO | 2004/026293 A2 | 4/2004 |
| WO | 2005/030794 A2 | 4/2005 |
| WO | 2009/052431 A2 | 4/2009 |
| WO | 2010/114940 A1 | 10/2010 |
| WO | 2013/173393 A1 | 11/2013 |
| WO | 2014/057436 A2 | 4/2014 |
| WO | 2014/107024 A1 | 7/2014 |
| WO | 2014/144871 A1 | 9/2014 |
| WO | 2015/095952 A1 | 7/2015 |

(Continued)

OTHER PUBLICATIONS

Talpir et al., "Hemiasterlin and Geodiamolide TA; Two New Cytotoxic Peptides from the Marine Sponge Hemiasterella Minor (Kirkpatrick)," Tetrahedron Letters, 35 (25): 4453-4456 (1994).

Zask et al., "D-piece modifications of the hemiasterlin analog HTI-286 produce potent tubulin inhibitors," Bioorganic & Medicinal Chemistry Letters, 14: 4353-4358 (2004).

Yamashita et al., "Synthesis and activity of novel analogs of hemiasterlin as inhibitors of tubulin polymerization: modification of the A segment," Bioorganic & Medicinal Chemistry Letters, 14: 5317-5322 (2004).

Nieman et al., "Synthesis and Antimitotic/Cytotoxic Activity of Hemiasterlin Analogues," Journal of Natural Products, 66: 183-199 (2003).

(Continued)

*Primary Examiner* — Matthew P Coughlin
*Assistant Examiner* — Ashli Ariana Chicks
(74) *Attorney, Agent, or Firm* — Morgan, Lewis & Bockius LLP

(57) ABSTRACT

A compound represented by formula (1):

[Chemical Formula 1]

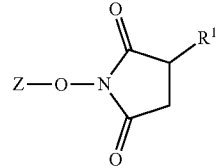

(1)

wherein
  $R^1$ represents a hydrogen atom or a sulfonyl group; and
  Z represents a group represented by formula (Z-1),
or a salt thereof.

14 Claims, No Drawings

(56) References Cited

FOREIGN PATENT DOCUMENTS

| WO | 2015/095953 A1 | 7/2015 |
| WO | 2015/128403 A2 | 9/2015 |
| WO | 2015/151079 A2 | 10/2015 |
| WO | 2016/072519 A1 | 5/2016 |
| WO | 2016/123582 A1 | 8/2016 |
| WO | 2019/031614 A1 | 2/2019 |
| WO | 2019/031615 A1 | 2/2019 |

OTHER PUBLICATIONS

Rocha-Lima et al., "A Phase 1 Trial of E7974 Administered on Day 1 of a 21-Day Cycle in Patients With Advanced Solid Tumors," Cancer, 4262-4270 (2012).

Doronina et al., "Enhanced Activity of Monomethylauristatin F through Monoclonal Antibody Delivery: Effects of Linker Technology on Efficacy and Toxicity," Bioconjugate Chemistry, 17 (1): 114-124 (2006).

Erickson et al., "Antibody-Maytansinoid Conjugates are Activated in Targeted Cancer Cells by Lysosomal Degradation and Linker-Dependent Intracellular Processing", Cancer Research, 66 (8): 4426-4433 (2006).

Zask et al., "Synthesis and Biological Activity of Analogues of the Antimicrotubule Agent N, B, B-Trimethyl-L-phenylalanyl-NI-[ (IS, 2E)-3-carboxy-1-isopropylbut-2-enyl]-NI, 3-dimethyl-L-valinamide (HTI-286)," Journal of Medicinal Chemistry, 47 (19): 4774-4786 (2004).

International Search Report issued in corresponding International Patent Application No. PCT/JP2020/005291 dated May 12, 2020.

International Preliminary Report on Patentability issued in corresponding International Patent Application No. PCT/JP2020/005291 dated Aug. 26, 2021.

International Search Report issued in corresponding International Patent Application No. PCT/JP2020/005369 dated Apr. 21, 2020.

International Search Report issued in corresponding International Patent Application No. PCT/JP2020/005307 dated May 12, 2020.

Alley et al., "Contribution of Linker Stability to the Activities of Anticancer Immunoconjugates," Bioconjugate Chemistry, 19: 759-765 (2008).

Baldwin et al., "Tunable Degradation of Maleimide-Thiol Adducts in Reducing Environments", Bioconjugate Chemistry, 22: 1946-1953 (2011).

International Search Report issued in corresponding International Patent Application No. PCT/JP2018/030143 dated Nov. 13, 2018.

Toki et al., "Protease-Mediated Fragmentation of p-Amidobenzyl Ethers: A New Strategy for the Activation of Anticancer Prodrugs," The Journal of Organic Chemistry, 67: 1866-1872 (2002).

International Search Report issued in corresponding International Patent Application No. PCT/JP2018/030144 dated Nov. 13, 2018.

* cited by examiner

HEMIASTERLIN DERIVATIVE AND ANTIBODY-DRUG CONJUGATE THEREOF

TECHNICAL FIELD

The present invention relates to hemiasterlin derivatives and antibody-drug conjugates thereof.

BACKGROUND ART

Hemiasterlin is a naturally occurring compound having a tripeptide structure, isolated from marine sponges, and is involved in microtubule depolymerization and mitotic arrest in cells (Non Patent Literature 1).

Several groups have so far conducted structural modification of hemiasterlin derivatives, and have found hemiasterlin derivatives exhibiting strong cytotoxicity and antimitotic effects for treatment for diseases such as cancer (Patent Literatures 1 to 5 and Non Patent Literatures 2 to 5). However, these hemiasterlin derivatives have been reported to be systemically delivered because of the lack of targeting properties, and exhibit cytotoxicity even to normal cells and show side effects (Non Patent Literature 6).

Antibody-drug conjugates are conjugates formed by conjugating an antibody and a drug directly or via an appropriate linker. Such antibody-drug conjugates have a characteristic to prevent systemic exposure to a drug and enhance the drug efficacy to target cells through delivering the drug to target cells via an antibody that binds to an antigen expressed on the target cells.

In addition, several groups have so far reported conjugates in which a hemiasterlin derivative having a maleimide group and a cysteine residue of an antibody or the like form thiosuccinimide (Patent Literatures 4 and 6 to 8).

CITATION LIST

Patent Literature

Patent Literature 1: International Publication No. WO 2004/026293
Patent Literature 2: International Publication No. WO 96/33211
Patent Literature 3: U.S. Pat. No. 7,579,323
Patent Literature 4: International Publication No. WO 2014/144871
Patent Literature 5: International Publication No. WO 2003/082268
Patent Literature 6: International Publication No. WO 2015/095952
Patent Literature 7: International Publication No. WO 2015/095953
Patent Literature 8: International Publication No. WO 2014/057436

Non Patent Literature

Non Patent Literature 1: Talpir, R. et al., Tetrahedron Lett., 1994, 35, 4453-4456.
Non Patent Literature 2: Zask, A. et. al., Bioorg. Med. Chem. Lett., 2004, 14, 4353-4358.
Non Patent Literature 3: Zask, A. et. al., J. Med. Chem., 2004, 47, 4774-4786.
Non Patent Literature 4: Yamashita, A. et. al., Bioorg. Med. Chem. Lett., 2004, 14, 5317-5322.
Non Patent Literature 5: Nieman, J. A. et. al., J, Nat. Prod., 2003, 66, 183-199.
Non Patent Literature 6: Rocha-Lima, C. M. et. al., Cancer, 2012, 118, 4262-4270.
Non Patent Literature 7: Doronina, S. O. et. al., Bioconjugate Chem., 2006, 17, 114-124.
Non Patent Literature 8: Erickson, H. K. et. al., Cancer Res., 2006, 66, 4426-4433.

SUMMARY OF INVENTION

Technical Problem

An object of the present invention is to provide an antibody-drug conjugate of a hemiasterlin derivative that provides cell damage specifically to target cells while suppressing cytotoxicity to normal cells.

Solution to Problem

As a result of diligent studies, the present inventors have found that an antibody-drug conjugate formed of a hemiasterlin derivative and an antibody and represented by formula (2) exhibits strong antitumor activity and has low cytotoxicity to normal cells, and that a hemiasterlin derivative represented by formula (1) is useful as a synthetic intermediate of the antibody-drug conjugate represented by formula (2), thereby completing the present invention.

That is, the present invention is as follows:

[Item 1]

A compound represented by formula (1):

[Chemical Formula 1]

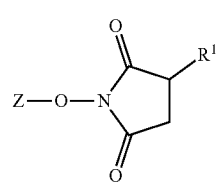

(1)

wherein $R^1$ represents a hydrogen atom or a sulfonyl group; and

Z represents a group represented by formula (Z-1), formula (Z-2) or formula (Z-3):

[Chemical Formula 2]

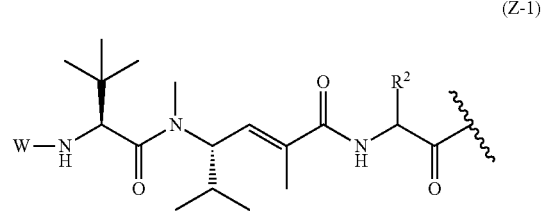

(Z-1)

-continued (Z-2)

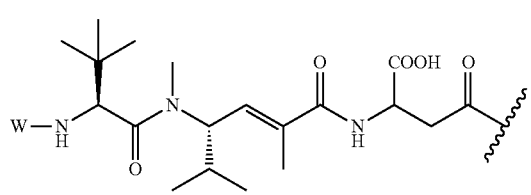

(Z-3)

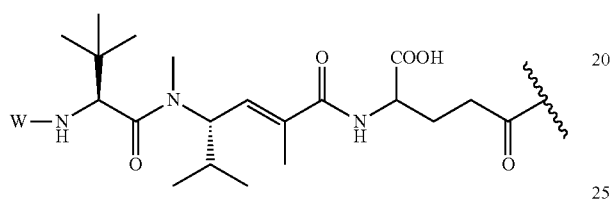

where
W represents a group represented by formula (W-1):

[Chemical Formula 3]

(W-1)

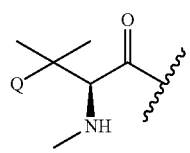

where
Q represents a group represented by formula (Q-1) or formula (Q-2):

[Chemical Formula 4]

(Q-1)

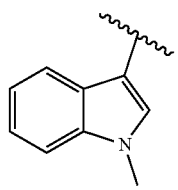

(Q-2)

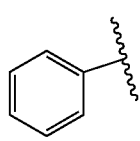

$R^2$ represents —$(CH_2)_u$—COOH; and
u represents 1 or 2,
or a salt thereof.

[Item 2]

The compound according to item 1, wherein $R^1$ is a hydrogen atom,
or a salt thereof.

[Item 3]

The compound according to item 1, selected from the following compound:

[Chemical Formula 5]

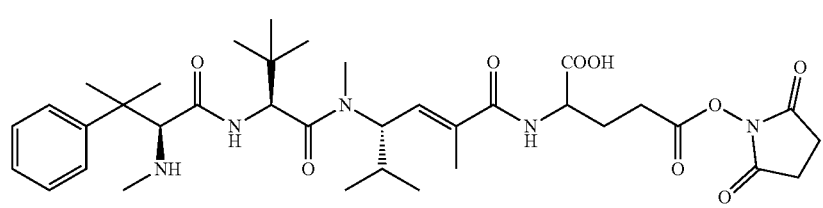

or a salt thereof.

[Item 4]

An antibody-drug conjugate represented by formula (2):

[Chemical Formula 6]

(2)

wherein mAb represents an antibody;

q represents an integer of 1 to 30; and

Z represents a group represented by formula (Z-1), formula (Z-2) or formula (Z-3):

[Chemical Formula 7]

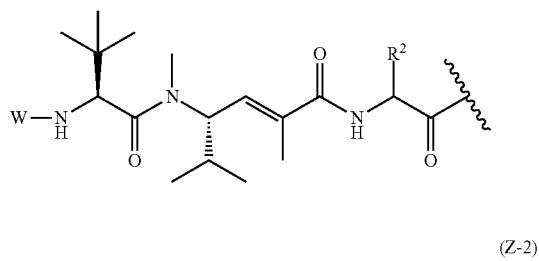
(Z-1)

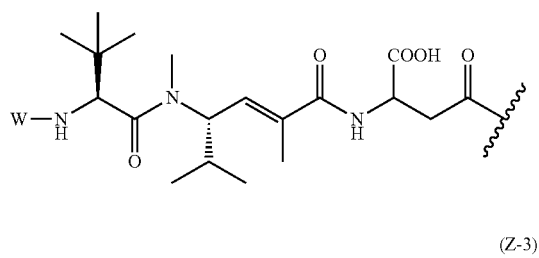
(Z-2)

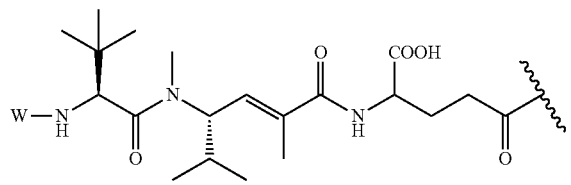
(Z-3)

where

W represents a group represented by formula (W-1):

[Chemical Formula 8]

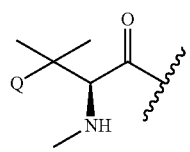
(W-1)

where

Q represents a group represented by formula (Q-1) or formula (Q-2):

[Chemical Formula 9]

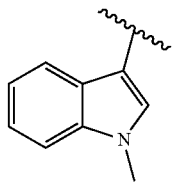
(Q-1)

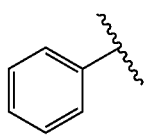
(Q-2)

$R^2$ represents $-(CH_2)_u-COOH$; and u represents 1 or 2, or a pharmaceutically acceptable salt thereof.

[Item 5]

The antibody-drug conjugate according to item 4, wherein mAb is brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, lorvotuzumab, rituximab, depatuxizumab, denintuzumab, enfortumab, telisotuzumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timiguttuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab, camidanlumab, cofetuzumab, ladiratuzumab, loncastuximab, telisotuzumab, enapotamab, an antibody of AMG 595 or anti-embigin antibody, or a pharmaceutically acceptable salt thereof.

[Item 6]
The antibody-drug conjugate according to item 4, wherein mAb is brentuximab,
or a pharmaceutically acceptable salt thereof.

[Item 7]
The antibody-drug conjugate according to any one of items 4 to 6, wherein q is an integer of 1 to 20,
or a pharmaceutically acceptable salt thereof.

[Item 8]
The antibody-drug conjugate according to any one of items 4 to 6, wherein q is an integer of 1 to 10,
or a pharmaceutically acceptable salt thereof.

[Item 9]
A pharmaceutical composition comprising the antibody-drug conjugate according to any one of items 4 to 8 or a pharmaceutically acceptable salt thereof.

[Item 10]
A pharmaceutical composition comprising:
the antibody-drug conjugate according to any one of items 4 to 8 or a pharmaceutically acceptable salt thereof; and
one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof.

[Item 11]
An anticancer agent comprising the antibody-drug conjugate according to any one of items 4 to 8, or a pharmaceutically acceptable salt thereof.

[Item 12]
The anticancer agent according to item 11, wherein cancer is breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma or leukemia.

[Item 13]
A method of treating cancer, comprising administering the antibody-drug conjugate according to any one of items 4 to 8 or a pharmaceutically acceptable salt thereof to a patient in need thereof.

[Item 14]
Use of the compound according to any one of items 1 to 3 or a salt thereof for producing an anticancer agent.

[Item 15]
Use of the antibody-drug conjugate according to any one of items 4 to 8 or a pharmaceutically acceptable salt thereof for producing an anticancer agent.

[Item 16]
The antibody-drug conjugate according to any one of items 4 to 8 or a pharmaceutically acceptable salt thereof for use in treatment of cancer.

[Item 17]
The antibody-drug conjugate according to any one of items 4 to 8 or a pharmaceutically acceptable salt thereof for use in combination with one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or a pharmaceutically acceptable salt thereof, to treat cancer.

Advantageous Effects of Invention

Antibody-drug conjugates formed of the hemiasterlin derivatives according to the present invention and antibodies exhibit cytotoxic activity specifically to antigen-expressing cells and have low cytotoxicity in normal cells other than the antigen-expressing cells, and therefore, can be anticancer agents excellent in safety.

DESCRIPTION OF EMBODIMENTS

In the present specification, the "alkyl group" means a linear, branched or cyclic saturated hydrocarbon group. Examples of the "alkyl group" preferably include a saturated hydrocarbon group having 1 to 6 carbon atoms. Specific examples of the "alkyl group" include, but are not limited to, a methyl group, an ethyl group, a propyl group, an isopropyl group, a butyl group, a 1,1-dimethylethyl group, a 1-methylpropyl group, a 2-methylpropyl group, a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a cyclopropyl group, a cyclobutyl group, a cyclopentyl group and a cyclohexyl group.

In the present specification, the "alkoxy group" means an oxy group substituted with an "alkyl group". Examples of the "alkoxy group" preferably include an oxy group substituted with a saturated hydrocarbon group having 1 to 6 carbon atoms. Specific examples of the "alkoxy group" include, but are not limited to, a methoxy group, an ethoxy group, a propoxy group, a 1-methylethoxy group, a butoxy group, a 1,1-dimethylethoxy group, a 1-methylpropoxy group, a 2-methylpropoxy group, a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a cyclopropoxy group, a cyclobutoxy group, a cyclopentyloxy group and a cyclohexyloxy group.

In the present specification, examples of the "halogen atom" include a fluorine atom, a chlorine atom, a bromine atom or an iodine atom. Preferably, examples thereof include a fluorine atom or a chlorine atom, and more preferably, examples thereof include a fluorine atom.

In the present specification, a hydrogen atom may be $^1H$ or $^2H(D)$. That is, for example, a deuterated product in which one or two or more $^1H$ of the compound represented by formula (1) are converted into $^2H(D)$ is also encompassed in the compound represented by formula (1).

A compound represented by formula (1) or a salt thereof (hereinafter, may be referred to as the "hemiasterlin derivative according to the present invention") is as follows:

[Chemical Formula 10]

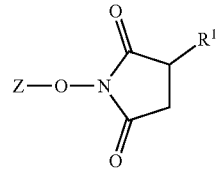

(1)

In the formula, $R^1$ represents a hydrogen atom or a sulfonyl group, and is preferably a hydrogen atom.

In the formula, Z represents a group represented by formula (Z-1), formula (Z-2) or formula (Z-3):

[Chemical Formula 11]

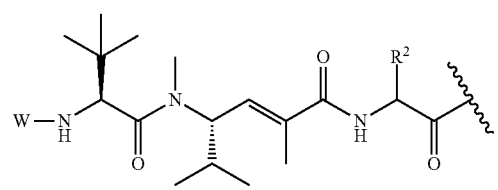

(Z-1)

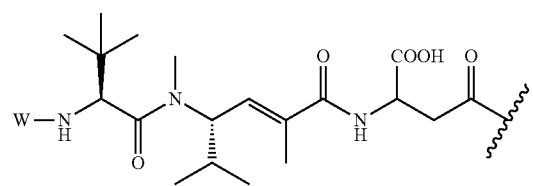

(Z-2)

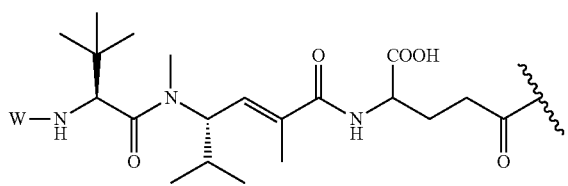

(Z-3)

The configuration of each of the carbon atom to which substituent $R^2$ is bonded in formula (Z-1) and the carbon atom to which the carboxyl group (—COOH) is bonded in formula (Z-2) and formula (Z-3) may be an S-form or an R-form.

In formula (Z-1), $R^2$ represents —(CH$_2$)$_u$—COOH. Here, u is an integer of 1 or 2. Examples of one aspect of u include 1, and examples of another aspect thereof include 2.

In formula (Z-1), formula (Z-2) or formula (Z-3), W represents a group represented by formula (W-1):

[Chemical Formula 12]

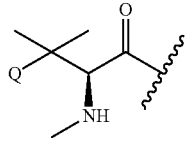

(W-1)

In formula (W-1), Q represents a group represented by formula (Q-1) or formula (Q-2):

[Chemical Formula 13]

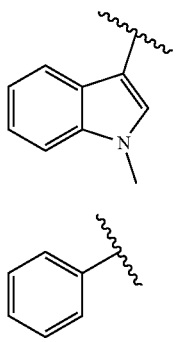

(Q-1)

(Q-2)

Examples of one aspect of Q include a group represented by formula (Q-1), and examples of another aspect thereof include a group represented by formula (Q-2).

Examples of one aspect of the hemiasterlin derivative according to the present invention include the following (1-A).

(1-A)
A compound, wherein, in formula (1),
R$^1$ is a hydrogen atom;
Z is a group represented by formula (Z-1), formula (Z-2) or formula (Z-3);
R$^2$ is —(CH$_2$)$_u$—COOH;
u is an integer of 1 or 2;
W is a group represented by formula (W-1); and
Q is a group represented by formula (Q-1), or a salt thereof.

Examples of one aspect of the hemiasterlin derivative according to the present invention include the following (1-B).

(1-B)
A compound, wherein, in formula (1),
R$^1$ is a hydrogen atom;
Z is a group represented by formula (Z-1), formula (Z-2) or formula (Z-3);
R$^2$ is —(CH$_2$)$_u$—COOH;
u is an integer of 1 or 2;
W is a group represented by formula (W-1); and
Q is a group represented by formula (Q-2), or a salt thereof.

Examples of one aspect of the hemiasterlin derivative according to the present invention include the following (1-C).

(1-C)
A compound, wherein, in formula (1),
R$^1$ is a hydrogen atom;
Z is a group represented by formula (Z-1);
R$^2$ is —(CH$_2$)$_u$—COOH;
u is an integer of 1 or 2;
W is a group represented by formula (W-1); and
Q is a group represented by formula (Q-1) or formula (Q-2), or a salt thereof.

Examples of one aspect of the hemiasterlin derivative according to the present invention include the following (1-D).

(1-D)
A compound, wherein, in formula (1),
R$^1$ is a hydrogen atom;
Z is a group represented by formula (Z-2);
W is a group represented by formula (W-1); and
Q is a group represented by formula (Q-1) or formula (Q-2), or a salt thereof.

Examples of one aspect of the hemiasterlin derivative according to the present invention include the following (1-E).

(1-E)
A compound, wherein, in formula (1),
R$^1$ is a hydrogen atom;
Z is a group represented by formula (Z-3);
W is a group represented by formula (W-1); and
Q is a group represented by formula (Q-1) or formula (Q-2), or a salt thereof.

An antibody-drug conjugate represented by formula (2), or a pharmaceutically acceptable salt thereof (hereinafter, may be referred to as the "antibody-drug conjugate according to the present invention") is, as shown below, a conjugate in which the antibody moiety derived from an antibody molecule and a drug moiety derived from a drug molecule are covalently bonded via a linker. In the present specification, the "antibody-drug conjugate" may be referred to as "ADC".

[Chemical Formula 14]

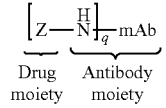

(2)

Drug moiety    Antibody moiety

Z of the drug moiety is as defined Z in a formula (1)
q indicates the drug antibody ratio (alternatively, referred to as DAR) in the antibody-drug conjugate. Drug antibody ratio q means the number of drug molecules per antibody molecule in one molecule of the antibody-drug conjugate, that is, per antibody-drug conjugate molecule. Note that antibody-drug conjugates obtained through chemical synthesis are often a mixture of a plurality of antibody-drug conjugate molecules that may have different drug antibody ratio q. In the present specification, the overall drug antibody ratio in such a mixture of antibody-drug conjugates (that is, the average value of drug antibody ratio q of each antibody-drug conjugate) is referred to as the "average drug antibody ratio" or "average DAR".

q is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. Examples of one aspect of q include an integer of 1 to 10; examples of another aspect thereof include an integer of 11 to 20; examples of another aspect thereof include an integer of 21 to 30; examples of another aspect thereof include an integer of 1 to 8; examples of another aspect thereof include an integer of 1 to 6; and examples of another aspect thereof include an integer of 1 to 4.

Examples of one aspect of the average DAR include 1 to 30; examples of another aspect thereof include 1 to 10; examples of another aspect thereof include 21 to 30; and examples of another aspect thereof include 21 to 30. Examples of another aspect thereof include 1 to 8, 1 to 2, 2 to 3, 3 to 4, 4 to 5, 6 to 7, 7 to 8, 8 to 9, 9 to 10, 5 to 15 and 15 to 25. It is possible to determine the average DAR by methods conventionally used to determine the average DAR, such as ultraviolet-visible-near-infrared spectroscopy, SDS-PAGE, mass spectrometry, ELISA (enzyme-linked immunosorbent assay) and HPLC (high performance liquid chromatography). It is possible to separate, purify and characterize an antibody-drug conjugate of a particular DAR from a mixture of a plurality of antibody-drug conjugates having different DARs by methods such as hydrophobic interaction chromatography (HIC) HPLC, reversed phase HPLC and electrophoresis.

mAb represents an "antibody". Here, it is sufficient that the "antibody" be an antibody including at least a heavy chain variable domain and a light chain variable domain, and it may be a complete antibody or a fragment of a complete antibody that is an antigen-binding fragment having an antigen-recognition site. The complete antibody has two full length light chains and two full length heavy chains, and respective light chains and heavy chains are linked by disulfide bonds. The complete antibody includes IgA, IgD, IgE, IgM and IgG, and IgG includes $IgG_1$, $IgG_2$, $IgG_3$ and $IgG_4$ as subtypes. In addition, it is preferable that the antibody be a monoclonal antibody. The antibody moiety and the drug moiety are linked via an F-amino group of a lysine residue in the antibody.

The antibody mAb is not particularly limited as long as it is an antibody that can recognize antigens present on the surface of target cells. It is sufficient that the target cell be a cell in need of treatment with a hemiasterlin derivative, and it is preferable that the target cell be a cancer cell. It is preferable that the antigen present on the surface of target cells be an antigen specific for the target cells, not expressed or expressed in a small amount in normal cells. Examples of one aspect of mAb include the known antibodies recited above; examples of another aspect thereof include brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, lorvotuzumab, rituximab, depatuxizumab, denintuzumab, enfortumab, telisotuzumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timiguatuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab, or anti-embigin antibody; examples of another aspect thereof include brentuximab, trastuzumab, inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab, or depatuxizumab; examples of another aspect thereof include brentuximab, trastuzumab, cetuximab; and examples of another aspect thereof include brentuximab or trastuzumab, preferably brentuximab.

Examples of mAb include anti-19A antibody, anti-AXL antibody, anti-BCMA antibody, anti-C4.4a antibody, anti-CA6 antibody, anti-CA9 antibody, anti-CA-125 antibody, anti-cadherin-6 antibody, anti-CD166 antibody, anti-CD19 antibody, anti-CD20 antibody, anti-CD22 antibody, anti-CD25 antibody, anti-CD27 antibody, anti-CD30 antibody, anti-CD33 antibody, anti-CD37 antibody, anti-CD40 antibody, anti-CD41 antibody, anti-CD44v6 antibody, anti-CD51 antibody, anti-CD52 antibody, anti-CD56 antibody, anti-CD70 antibody, anti-CD74 antibody, anti-CD79 antibody, anti-CD79b antibody, anti-CEACAM5 antibody, anti-c-Met antibody, anti-DLL3 antibody, anti-DPEP3 antibody, anti-EGFR antibody, anti-EGFRvIII antibody, anti-ENPP3 antibody, anti-EpCAM antibody, anti-EphA4 antibody, anti-FGFR2 antibody, anti-FGFR3 antibody, anti-FTL3 antibody, anti-folate receptor a antibody, anti-gripican 3 antibody, anti-gpN1VIB antibody, anti-HER2 antibody, anti-HER3 antibody, anti-IL-3RA antibody, anti-LAMP1 antibody, anti-LIV-1 antibody, anti-LRRC15 antibody, anti-Ly6E antibody, anti-mesothelin antibody, anti-MUC-16 antibody, anti-NaPi2b antibody, anti-nectin-4 antibody, anti-CD352 antibody, anti-β-cadherin antibody, anti-PMSA antibody, anti-protein tyrosine kinase 7 antibody, anti-SLITRK antibody, anti-STEAP1 antibody, anti-CD138 antibody, anti-tissue factor antibody, anti-CD71 antibody, anti-TIM-1 antibody, anti-Trop2 antibody, anti-5T4 antibody, anti-B7-H3 antibody, anti-CD163 macrophage receptor antibody, anti-CD38 antibody, anti-CD48 antibody, anti-cKit antibody, anti-guanylate cyclase C antibody, anti-gastrin releasing peptide antibody, anti-solute carrier antibody, anti-tumor-associated MUC-1 antibody, anti-GD2 antibody, anti-α4β7 integrin antibody or anti-embigin antibody. Examples of another aspect of mAb include anti-CD19 antibody, anti-CD20 antibody, anti-CD22 antibody, anti-CD30 antibody, anti-CD33 antibody, anti-CD52 antibody, anti-CD70 antibody, anti-CD79b antibody, anti-CEACAM5 antibody, anti-EGFR antibody, anti-EGFRvIII antibody, anti-gpNM4B antibody, anti-IER2 antibody, anti-mesothelin antibody, anti-CD138 antibody, anti-CD38 antibody or anti-GD2 antibody. Examples of another aspect of mAb include anti-CD19 antibody, anti-CD20 antibody, anti-CD22 antibody, anti-CD30 antibody, anti-CD33 antibody, anti-CD52 antibody, anti-CD79b antibody, anti-CEACAM5 antibody, anti-EGFR antibody, anti-EGFRvIII antibody, anti-gpNMIB antibody, anti-HER2 antibody, anti-mesothelin antibody or anti-CD138 antibody.

The "antibody of AMG 595" means anti-EGFRvIII antibody that can be obtained by the method described in Mol. Cancer Ther., 2015, 14, 1614-1624.

Examples of one aspect of the antibody-drug conjugate according to the present invention include the following (2-A).

(2-A)

An antibody-drug conjugate, wherein, in formula (2),
mAb is brentuximab or trastuzumab;
q is an integer of 1 to 8;
Z is a group represented by formula (Z-1), formula (Z-2) or formula (Z-3);
$R^2$ is —$(CH_2)_u$—COOH;
u is an integer of 1 or 2;
W is a group represented by formula (W-1); and
Q is a group represented by formula (Q-1),
or a pharmaceutically acceptable salt thereof.

Examples of one aspect of the antibody-drug conjugate according to the present invention include the following (2-B).

(2-B)

An antibody-drug conjugate, wherein, in formula (2),
mAb is brentuximab or trastuzumab;
q is an integer of 1 to 8;
Z is a group represented by formula (Z-1), formula (Z-2) or formula (Z-3);
$R^2$ is —$(CH_2)_u$—COOH;
u is an integer of 1 or 2;
W is a group represented by formula (W-1); and
Q is a group represented by formula (Q-2),
or a pharmaceutically acceptable salt thereof.

Examples of one aspect of the antibody-drug conjugate according to the present invention include the following (2-C).

(2-C)

An antibody-drug conjugate, wherein, in formula (2),
mAb is brentuximab or trastuzumab;
q is an integer of 1 to 8;
Z is a group represented by formula (Z-1);
$R^2$ is —$(CH_2)_u$—COOH;
u is an integer of 1 or 2;
W is a group represented by formula (W-1); and
Q is a group represented by formula (Q-1) or formula (Q-2),
or a pharmaceutically acceptable salt thereof.

Examples of one aspect of the antibody-drug conjugate according to the present invention include the following (2-D).

(2-D)

An antibody-drug conjugate, wherein, in formula (2),
mAb is brentuximab or trastuzumab;
q is an integer of 1 to 8;
Z is a group represented by formula (Z-2);
W is a group represented by formula (W-1);
Q is a group represented by formula (Q-1) or formula (Q-2);
or a pharmaceutically acceptable salt thereof.

Examples of one aspect of the antibody-drug conjugate according to the present invention include the following (2-E).

(2-E)

An antibody-drug conjugate, wherein, in formula (2),
mAb is brentuximab or trastuzumab;
q is an integer of 1 to 8;
Z is a group represented by formula (Z-3);
W is a group represented by formula (W-1);
Q is a group represented by formula (Q-1) or formula (Q-2);

or a pharmaceutically acceptable salt thereof.

In general, it is possible to carry out production and analysis of the antibody-drug conjugate by an arbitrary technique known to a person having ordinary skill in the art. Examples of such a method include the method described in Antibody-Drug Conjugates (edited by Laurent Ducry, published by Humana Press, 2013).

The antibody-drug conjugate may be formed by, for example, reacting the ε-amino group of a lysine residue in the antibody with a hemiasterlin derivative.

The antibody-drug conjugate undergoes metabolism of the antibody in target cells (antigen-expressing cells), and a structure including a part of the antibody (antibody fragment) and the drug moiety may be released as an active metabolite. For example, it is disclosed in Non Patent Literature 7 that the Cys-drug moiety of an antibody-drug conjugate is released in cells through metabolism of the antibody. In addition, it is disclosed in Non Patent Literature 8 that the Lys-drug moiety of an antibody-drug conjugate is released in cells through metabolism of the antibody.

It is speculated that the antibody-drug conjugate is delivered specifically into particular antigen-expressing cells through uptake into cells utilizing antibody-antigen reaction, and then releases the active metabolite through the mechanisms mentioned above, thereby exerting drug efficacy only in the particular cells. The antibody-drug conjugate can be taken up specifically into cancer cells, and therefore, can be expected to exert strong drug efficacy against cancer cells.

On the other hand, it is believed that some antibody-drug conjugates may be broken down by protease or the like contained in the blood before being delivered to target cells, releasing the active metabolite into the blood. At that time, in case of conventional antibody-drug conjugates, the active metabolite released in the blood acts also on normal cells. As a result, unintentional systemic exposure is caused, which is unfavorable because side effects tend to occur.

Further, after being specifically delivered into particular antigen-expressing cells, the antibody-drug conjugate releases the active metabolite through the above-described mechanism, and as a result the active metabolite may be released from the inside of the cells to the outside of the cells or into the blood through cell death or the like. At that time, in case of conventional antibody-drug conjugates, the active metabolite released in the blood acts also on normal cells. As a result, unintentional systemic exposure is caused, which is unfavorable because side effects tend to occur.

In contrast, the active metabolite that is released from the antibody-drug conjugate according to the present invention, as reported in Non Patent Literature 7 or Non Patent Literature 8, is unlikely to act on normal cells and is quickly metabolized and excreted, even if the active metabolite is released in the blood before or after reaching target cells; therefore, it can be expected that side effects due to systemic exposure is small.

That is, because of being produced through metabolism of the antibody-drug conjugate according to the present invention, the active metabolite is expected to exert drug efficacy specifically to cancer cells, and also to have small influence on normal cells and high safety.

In the present specification, except when it is particularly necessary to make distinction, the three letter abbreviated notations shown below may be used for representing both α-amino acids and corresponding amino acid residues. In addition, the optical activity of the α-amino acids may include any of DL form, D form and L form unless otherwise specified. For example, "glutamic acid" or "Glu" represents DL-glutamic acid or a residue thereof, D-glutamic acid or a residue thereof, or L-glutamic acid or a residue thereof.

The "salt" is a suitable salt of the hemiasterlin derivative according to the present invention and is acceptable as a pharmaceutical raw material, and is preferably a common non-toxic salt. For the "salt", for example, in addition to acid addition salts such as organic acid salts (for example, acetate, trifluoroacetate, maleate, fumarate, citrate, tartrate, methanesulfonate, benzenesulfonate, formate, p-toluenesulfonate or the like) and inorganic acid salts (for example, hydrochloride, hydrobromide, hydroiodide, sulfate, nitrate, phosphate or the like); salts with amino acids (for example, arginine, aspartic acid, glutamic acid or the like); metal salts such as alkali metal salts (for example, sodium salt, potassium salt or the like) and alkaline earth metal salts (for example, calcium salt, magnesium salt or the like); ammonium salts; or organic base salts (for example, trimethylamine salt, triethylamine salt, pyridine salt, picoline salt, dicyclohexylamine salt, N,N'-dibenzylethylenediamine salt or the like), a person having ordinary skill in the art may select appropriate salts as appropriate.

Examples of the "pharmaceutically acceptable salt" include acid addition salts and base addition salts. Examples of the acid addition salt include inorganic acid salts such as hydrochloride, hydrobromide, sulfate, hydroiodide, nitrate and phosphate, or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate and camphorsulfonate. In addition, examples of the base addition salt include inorganic base salts such as sodium salt, potassium salt, calcium salt, magnesium salt, barium salt and aluminum salt, or organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine and N,N-dibenzylethylamine. Furthermore, examples of the "pharmaceutically acceptable salt" include salts (amino acid salts) with basic amino acids or acidic amino acids such as arginine, lysine, ornithine, aspartic acid and glutamic acid.

When it is desired to acquire a salt of the hemiasterlin derivative or antibody-drug conjugate according to the present invention, if the target compound is obtained in the form of salt, that compound may be purified as is, and if the target compound is obtained in the free form, that compound may be dissolved or suspended in an appropriate organic solvent, to which an acid or base is added to form a salt by a conventional method.

The hemiasterlin derivative and antibody-drug conjugate according to the present invention may be present in the form of hydrates and/or solvates (ethanolate and the like) with various solvents, and these hydrates and/or solvates are also included in the hemiasterlin derivative and antibody-drug conjugate according to the present invention. Furthermore, all modes of crystal forms of the hemiasterlin derivative and antibody-drug conjugate according to the present invention are also included in the present invention.

Among the hemiasterlin derivative and antibody-drug conjugate according to the present invention, some may have optical isomers based on the optically active center, atropisomers based on axial or planar chirality caused by restraint of intramolecular rotation, and all of the other stereoisomers, tautomers and geometrical isomers, and all possible isomers including the above are encompassed within the scope of the present invention.

In particular, optical isomers and atropisomers may be obtained as racemate, and when optically active starting materials or intermediates are used, optically active substances may be obtained respectively. If necessary, at an appropriate stage in the following production methods, corresponding raw material, intermediate or racemate, the final product, may be optically resolved into optical enantiomers physically or chemically through known separation methods such as a method using an optically active column and fractional crystallization method. Specifically, for example, in diastereomer method, two diastereomers are formed from racemate through a reaction using an optically active resolving agent. In general, these different diastereomers have different physical properties, and thus, can be optically resolved by known methods such as fractional crystallization.

Production methods for the hemiasterlin derivative and antibody-drug conjugate according to the present invention will be mentioned below. The hemiasterlin derivative according to the present invention represented by formula (1) may be produced by, for example, the following production method A to C.

Production Method A

When Z is a group represented by formula (Z-1); W is a group represented by formula (W-1); Q is a group represented by formula (Q-1); and $R^1$ is a hydrogen atom, the compound represented by formula (1) may be produced by, for example, the following production method:

[Chemical Formula 15]

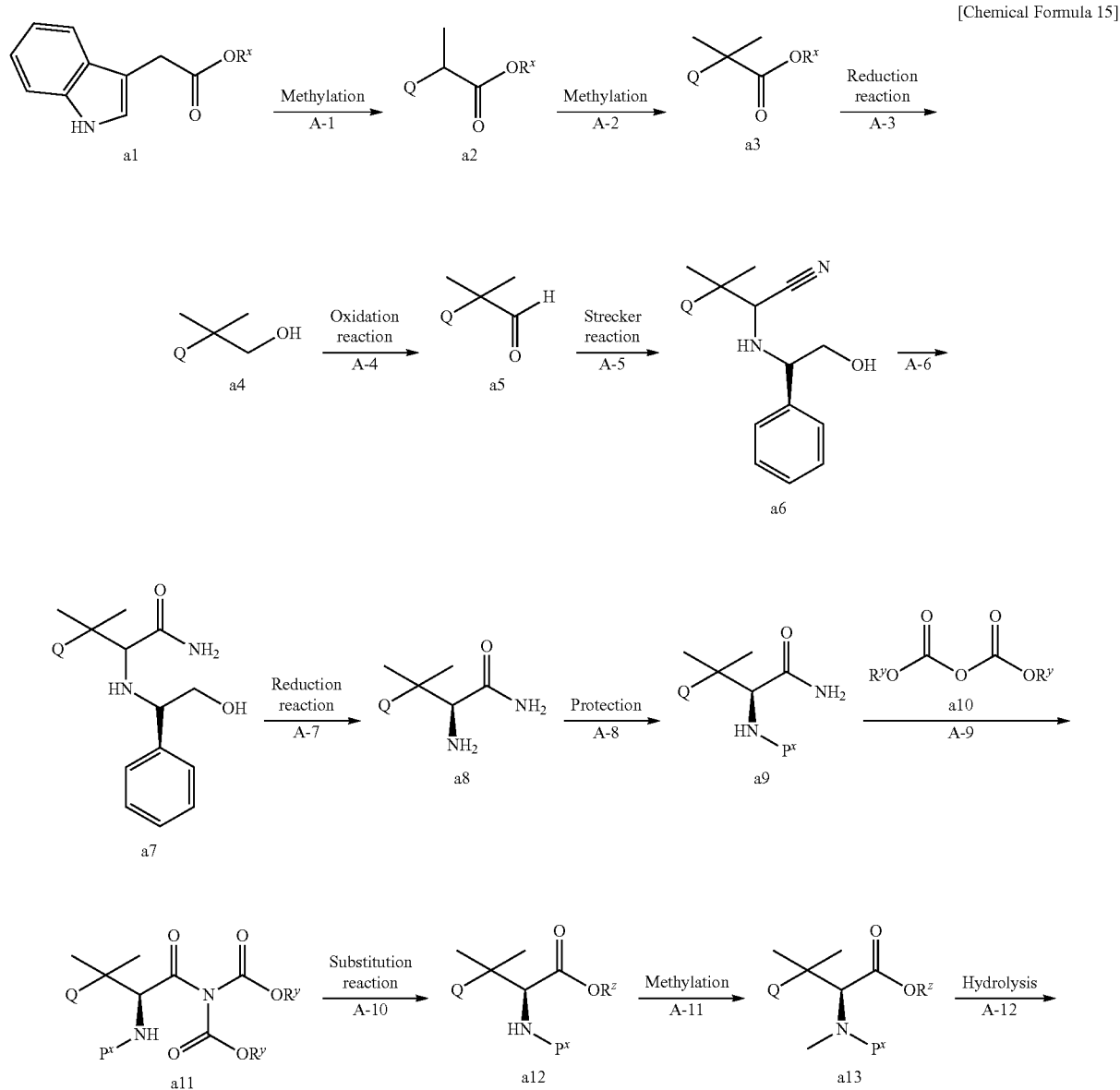

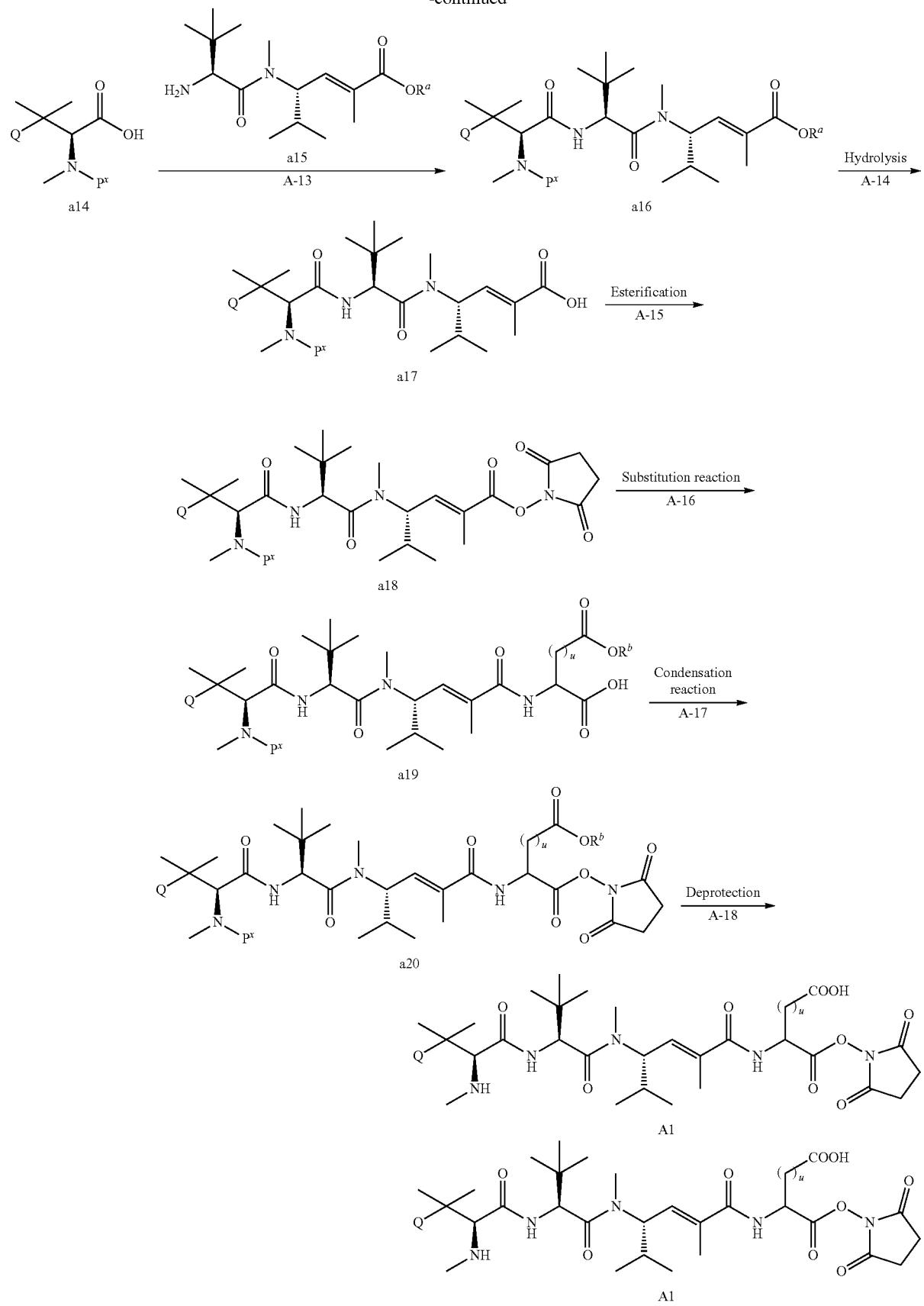

wherein, a is as defined in item 1; $R^a$, W, $R^x$, $R^y$ and $R^z$ each independently represent a $C_{1-6}$ alkyl group or a benzyl group; and $P^X$ represents a protecting group for the amino group.

As the above protecting group for the amino group, represented by $P^X$, the protecting groups described in Protective Groups in Organic Synthesis (authored by Theodora W. Greene, Peter G. M. Wuts, issued by John Wiley & Sons, Inc., 1999) and the like may be used.

Compound a1 may be produced by the method described in, for example, J. Med. Chem., 2007, 50, 4329-4339 and the like, or may be purchased as a commercial product. Compound a15 may be produced by the method described in, for example, Tetrahedron Lett., 1997, 38, 317-320 and the like, or may be purchased as a commercial product.

[A-1 Step]

Compound a2 may be produced by allowing compound a1 to react with various methylating reagents in an appropriate solvent in the presence of an appropriate base. Examples of the methylating reagent include methyl halide, and preferably include methyl iodide, methyl bromide and methyl chloride. Examples of the base preferably include potassium hexamethyldisilazide. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C. This step may be carried out in accordance with the method described in J. Nat. Prod. 2003, 66, 183-199 and the like.

[A-2 Step]

Compound a3 may be produced from compound a2 in accordance with the method described in the above A-1 step.

[A-3 Step]

Compound a4 may be produced by allowing compound a3 to react with an appropriate reducing agent in an appropriate solvent. The reducing agent is selected from reducing agents used in usual organic synthesis reactions as appropriate, and examples thereof preferably include diisobutylaluminum hydride. Examples of the solvent preferably include diethyl ether. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-4 Step]

Compound a5 may be produced by oxidizing compound a4 using an appropriate oxidizing agent in an appropriate solvent. The oxidizing agent may be selected from oxidizing agents used in usual organic synthesis reactions as appropriate, and examples thereof preferably include tetrapropylammonium perruthenate. Examples of the solvent preferably include dichloromethane. The reaction time is normally 5 minutes to 72 hours, and is preferably 30 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-5 Step]

Compound a6 may be produced by α-aminocyanating the aldehyde of the compound a5 in an appropriate solvent. Examples of the solvent preferably include toluene and dichloromethane. The reaction time is normally 5 minutes to 96 hours, and is preferably 24 hours to 72 hours. The reaction temperature is normally 0° C. to 200° C., and is preferably 0° C. to 100° C. This step may be carried out in accordance with the method described in Org. Lett. 2002, 4, 695-697 and the like.

[A-6 Step]

Compound a7 may be produced from compound a6 by using an appropriate oxidizing agent in an appropriate solvent in the presence of or in the absence of an appropriate base. The oxidizing agent may be selected from oxidizing agents used in usual organic synthesis reactions as appropriate, and examples thereof preferably include hydrogen peroxide. Examples of the base preferably include potassium carbonate. Examples of the solvent preferably include methanol. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Org. Chem. 2001, 66, 7355-7364 and the like.

[A-7 Step]

Compound a8 may be produced by reducing compound a7 using an appropriate reducing agent in an appropriate solvent in the presence of an appropriate catalyst. The reducing agent may be selected from reducing agents used in usual organic synthesis reactions as appropriate, and examples thereof preferably include hydrogen, formate such as ammonium formate, or hydrazine. Examples of the catalyst include transition metals such as palladium, nickel, rhodium, cobalt and platinum, salts thereof or complexes thereof, or supports such as polymer having the above transition metals supported thereon. Examples of the solvent preferably include ethanol or methanol. The reaction time is normally 5 minutes to 72 hours, and is preferably 30 minutes to 24 hours. The reaction temperature is normally 0° C. to 200° C., and is preferably 0° C. to 100° C. This step may be carried out in accordance with the method described in J. Org. Chem. 2001, 66, 7355-7364 and the like.

[A-8 Step]

Compound a9 may be produced by protecting the amino group of compound a8 with protecting group $P^X$. This step may be carried out in accordance with the method described in Protective Groups in Organic Synthesis (authored by Theodora W. Greene, Peter G. M. Wuts, issued by John Wiley & Sons, Inc., 1999) and the like.

[A-9 Step]

Compound a11 may be produced by allowing compound a9 to react with various acylating reagents (for example, compound a10) in an appropriate solvent in the presence of or in the absence of an appropriate base. Examples of the acylating reagent include carboxylic halide and carboxylic anhydride, and preferably include di-tert-butyl dicarbonate. Examples of the base preferably include diisopropylethylamine. Examples of the solvent preferably include chloroform. The reaction time is normally 5 minutes to 72 hours, and is preferably 30 minutes to 24 hours. The reaction temperature is normally 0° C. to 200° C., and is preferably 0° C. to 50° C.

[A-10 Step]

Compound a12 may be produced by allowing compound a11 to react with an appropriate alkali metal alkoxide in an appropriate solvent. The alkali metal alkoxide may be selected from alkali metal alkoxides used in usual organic synthesis reactions as appropriate, and examples thereof preferably include lithium methoxide or lithium ethoxide. Examples of the solvent preferably include methanol or ethanol. The reaction time is normally 5 minutes to 72 hours, and is preferably 30 minutes to 6 hours. The reaction temperature is normally −78° C. to 200° C., and is preferably −78° C. to 50° C.

[A-11 Step]

Compound a13 may be produced by allowing compound a12 to react with various methylating reagents in an appropriate solvent in the presence of an appropriate base. Examples of the methylating reagent include methyl halide, and preferably include methyl iodide, methyl bromide and methyl chloride. Examples of the base preferably include sodium hydride. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C.

[A-12 Step]

Compound a14 may be produced by hydrolyzing the ester of compound a13, in an appropriate solvent in the presence of an appropriate base. Examples of the base preferably include lithium hydroxide. Examples of the solvent preferably include water or methanol. The reaction time is normally 5 minutes to 72 hours, and is preferably 30 minutes to 24 hours. The reaction temperature is normally 0° C. to 200° C., and is preferably 0° C. to 100° C.

[A-13 Step]

Compound a16 may be produced by condensing compound a14 and compound a15 using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide or bromotripyrrolidinophosphonium hexafluorophosphate. In addition a carbonyl activating reagent such as 1-hydroxybenzotriazole may be used together as necessary, in order to improve efficiency of the condensation reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C. This step may be carried out in accordance with the method described in Tetrahedron Lett., 1997, 38, 317-320 and the like.

[A-14 Step]

Compound a17 may be produced by hydrolyzing the ester of compound a16, in accordance with the method described in the above A-12 step. This step may be carried out in accordance with the method described in Tetrahedron Lett., 1997, 38, 317-320 and the like.

[A-15 Step]

Compound a18 may be produced by allowing compound a17 to react with N-hydroxysuccinimide using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide, or bromotripyrrolidinophosphonium hexafluorophosphate. In addition, a carbonyl activating reagent such as 1-hydroxybenzotriazole may be used together as necessary, in order to improve efficiency of the reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C.

[A-16 Step]

Compound a19 may be produced by allowing compound a18 to react with an ester of an amino acid or peptide in an appropriate solvent in the presence of an appropriate base. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally 0° C. to 200° C., and is preferably 0° C. to 100° C.

[A-17 Step]

Compound a20 may be produced by condensing compound a19 in accordance with the method described in the above A-15 step.

[A-18 Step]

Compound A1 may be produced by deprotection of the protecting group $P^x$ for the amino group of compound a20 and hydrolysis of the ester (—COOR$^b$). This step may be carried out in accordance with the method described in Protective Groups in Organic Synthesis (authored by Theodora W. Greene, Peter G. M. Wuts, issued by John Wiley & Sons, Inc., 1999) and the like.

Production Method B

When Z is a group represented by formula (Z-1); W is a group represented by formula (W-1); Q is a group represented by formula (Q-2); and $R^1$ is a hydrogen atom, the compound represented by formula (1) may be produced by, for example, the following production method:

[Chemical Formula 16]

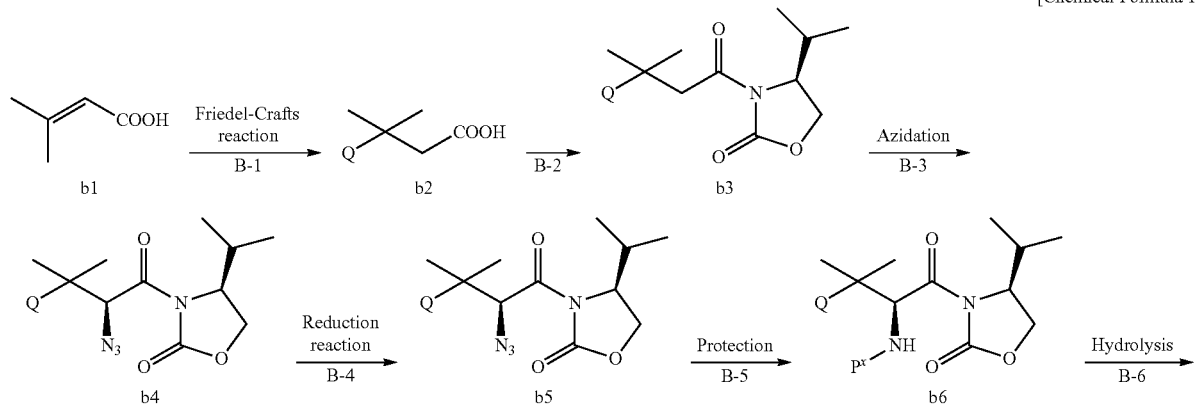

-continued
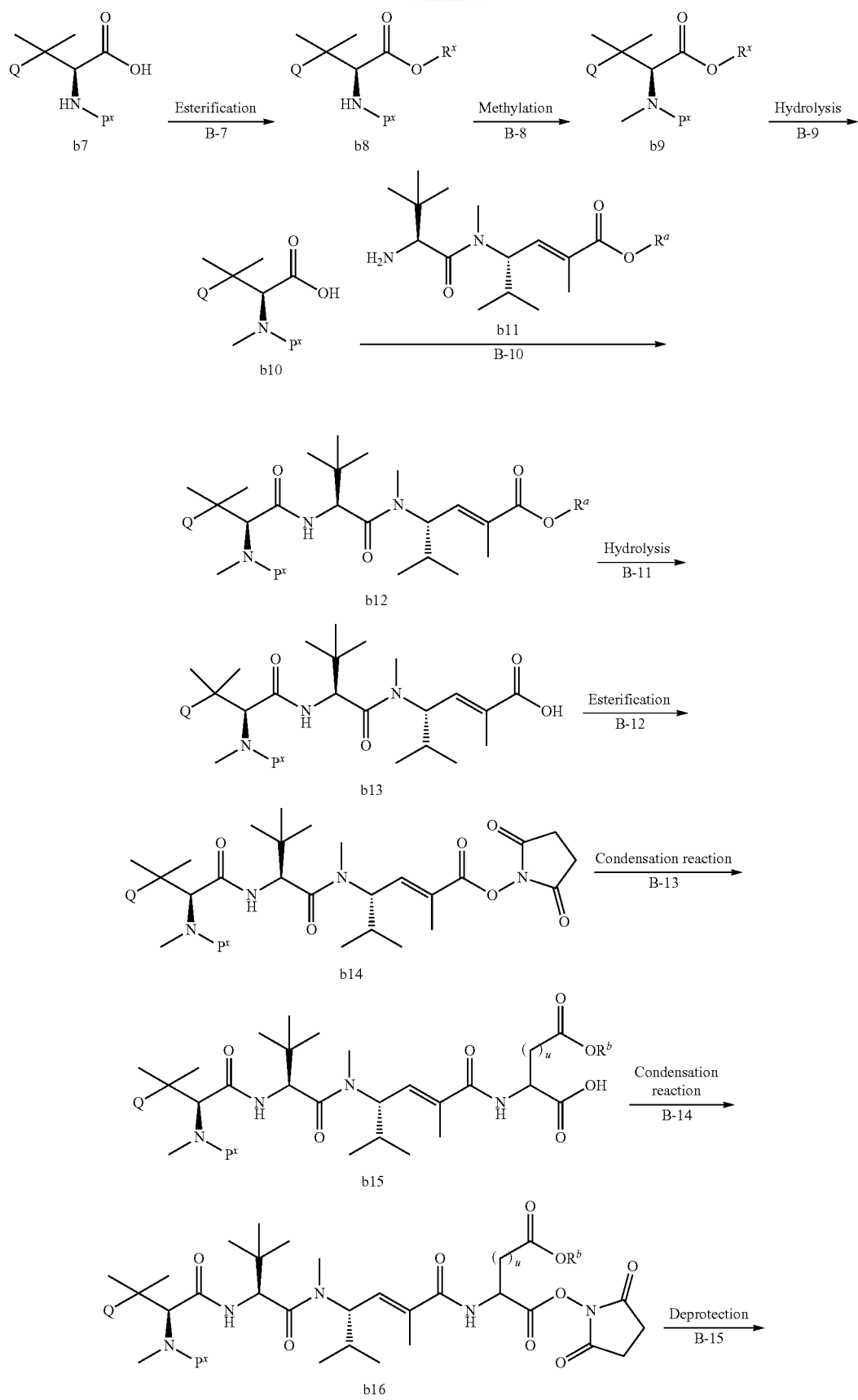

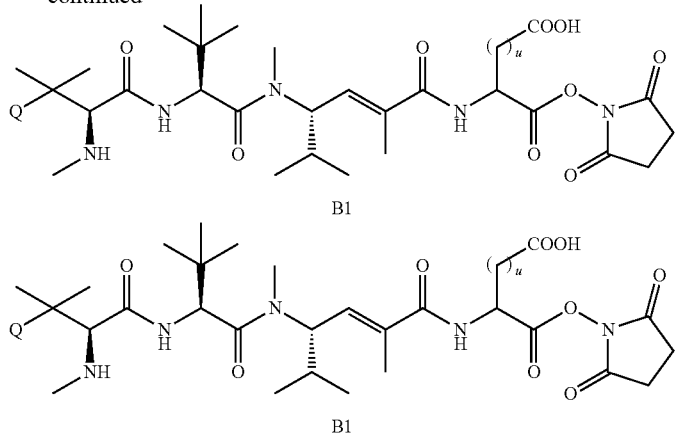

B1

B1 wherein, a is as defined in item 1; $R^a$, W and $R^X$ each represent a $C_{1-6}$ alkyl group or a benzyl group; and $P^X$ means a protecting group for the amino group.

Compound b1 may be, for example, purchased as a commercial product. Compound b11 may be produced by the method described in, for example, Tetrahedron Lett., 1997, 38, 317-320 and the like, or may be purchased as a commercial product.

[B-1 Step]

Compound b2 may be produced by allowing compound b1 to react with benzene in the presence of various Lewis acids. Examples of the Lewis acid include boron halide, aluminum halide, gallium halide, iron halide and titanium halide, and preferably include aluminum chloride and iron chloride. The reaction time is normally 5 minutes to 48 hours, and is preferably 30 minutes to 4 hours. The reaction temperature is normally −78° C. to 200° C., and is preferably 50° C. to 150° C. This step may be carried out in accordance with the method described in J. Nat. Prod. 2003, 66, 183-199 and the like.

[B-2 Step]

Compound b3 may be produced by allowing compound b2 to react with various carboxylic halides and then to react with an alkali metallized 4-alkyl-2-oxazolidinone in an appropriate solvent in the presence of an appropriate base. Examples of the base preferably include triethylamine or diisopropylethylamine. Examples of the solvent preferably include tetrahydrofuran. Examples of the carboxylic halide include carboxylic chloride, and preferably include pivaloyl chloride. Examples of the alkali metallized 4-alkyl-2-oxazolidinone include 4-alkyl-2-oxazolidinone lithium and 4-alkyl-2-oxazolidinone sodium, and preferably include 4-isopropyl-2-oxazolidinone lithium. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[B-3 Step]

Compound b4 may be produced by allowing compound b3 to react with various azidating reagents in an appropriate solvent in the presence of an appropriate base. Examples of the azidating reagent include sodium azide, trimethylsilyl azide and diphenylphosphoryl azide, and preferably include trimethylsilyl azide. Examples of the base preferably include potassium hexamethyldisilazide. Examples of the solvent preferably include tetrahydrofuran. The reaction time is normally 5 minutes to 72 hours, and is preferably 30 minutes to 24 hours. The reaction temperature is normally −78° C. to 200° C., and is preferably −78° C. to 75° C. This step may be carried out in accordance with the method described in J. Nat. Prod. 2003, 66, 183-199 and the like.

[B-4 Step]

Compound b5 may be produced from compound b4 in accordance with the method described in the above A-7 step.

[B-5 Step]

Compound b6 may be produced from compound b5 in accordance with the method described in the above A-8 step.

[B-6 Step]

Compound b7 may be produced from compound b6 by using an appropriate oxidizing agent in an appropriate solvent in the presence of an appropriate base. Examples of the base preferably include lithium hydroxide. Examples of the solvent preferably include methanol, tetrahydrofuran or water. The oxidizing agent may be selected from oxidizing agents used in usual organic synthesis reactions as appropriate, and examples thereof preferably include hydrogen peroxide. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Nat. Prod. 2003, 66, 183-199 and the like.

[B-7 Step]

Compound b8 may be produced by allowing compound b7 to react with various alkylating reagents in an appropriate solvent in the presence of an appropriate base. Examples of the alkylating reagent include alkyl halide, and preferably include alkyl iodide, alkyl bromide and alkyl chloride. Examples of the base preferably include sodium carbonate and potassium carbonate. Examples of the solvent preferably include N,N-dimethylformamide. The reaction time is normally 5 minutes to 48 hours, and is preferably 10 minutes to 2 hours. The reaction temperature is normally −78° C. to 100° C., and is preferably −10° C. to 25° C. This step may be carried out in accordance with the method described in Protective Groups in Organic Synthesis (authored by Theodora W. Greene, Peter G. M. Wuts, issued by John Wiley & Sons, Inc., 1999) and the like.

[B-8 Step]

Compound b9 may be produced from compound b8 in accordance with the method described in the above A-11 step.

31

[B-9 Step]

Compound b10 may be produced from compound b9 in accordance with the method described in the above A-12 step.

[B-10 Step]

Compound b12 may be produced from compound b10 and compound b11 in accordance with the method described in the above A-13 step.

[B-11 Step]

Compound b13 may be produced by hydrolyzing the ester of compound b12 in accordance with the method described in the above A-12 step.

[B-12 Step]

Compound b14 may be produced from compound b13 in accordance with the method described in the above A-15 step.

[B-13 Step]

Compound b15 may be produced from compound b14 in accordance with the method described in the above A-16 step.

[B-14 Step]

Compound b16 may be produced from compound b15 in accordance with the method described in the above A-17 step.

32

[B-15 Step]

Compound B1 may be produced from compound b16 in accordance with the method described in the above A-18 step.

Production Method C

When Z is a group represented by formula (Z-2) or formula (Z-3); W is a group represented by formula (W-1); and $R^1$ is a hydrogen atom, the compound represented by formula (1) may be produced by, for example, the following production method:

[Chemical Formula 17]

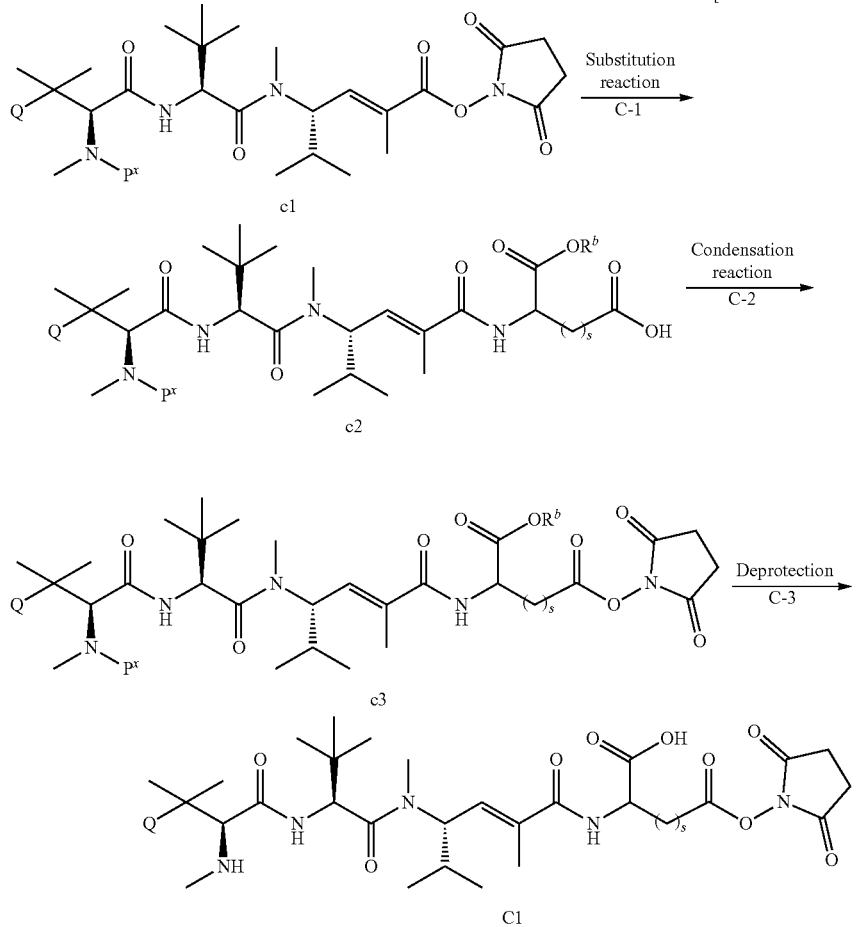

wherein, s represents 1 or 2; and $R^b$ and $P^X$ are as defined above.

Compound c1 represents compound a18 of Production Method A or compound b14 of Production Method B.

[C-1 Step]

Compound c2 may be produced from compound c1 in accordance with the method described in the above A-16 step.

[C-2 Step]

Compound c3 may be produced from compound c2 in accordance with the method described in the above A-17 step.

[C-3 Step]

Compound C1 may be produced from compound c3 in accordance with the method described in the above A-18 step.

Production Method E

When Z is a group represented by formula (Z-2) or formula (Z-3); W is a group represented by formula (W-1); and $R^1$ is a hydrogen atom, the compound represented by formula (1) may be produced by, for example, the following production method:

[Chemical Formula 18]

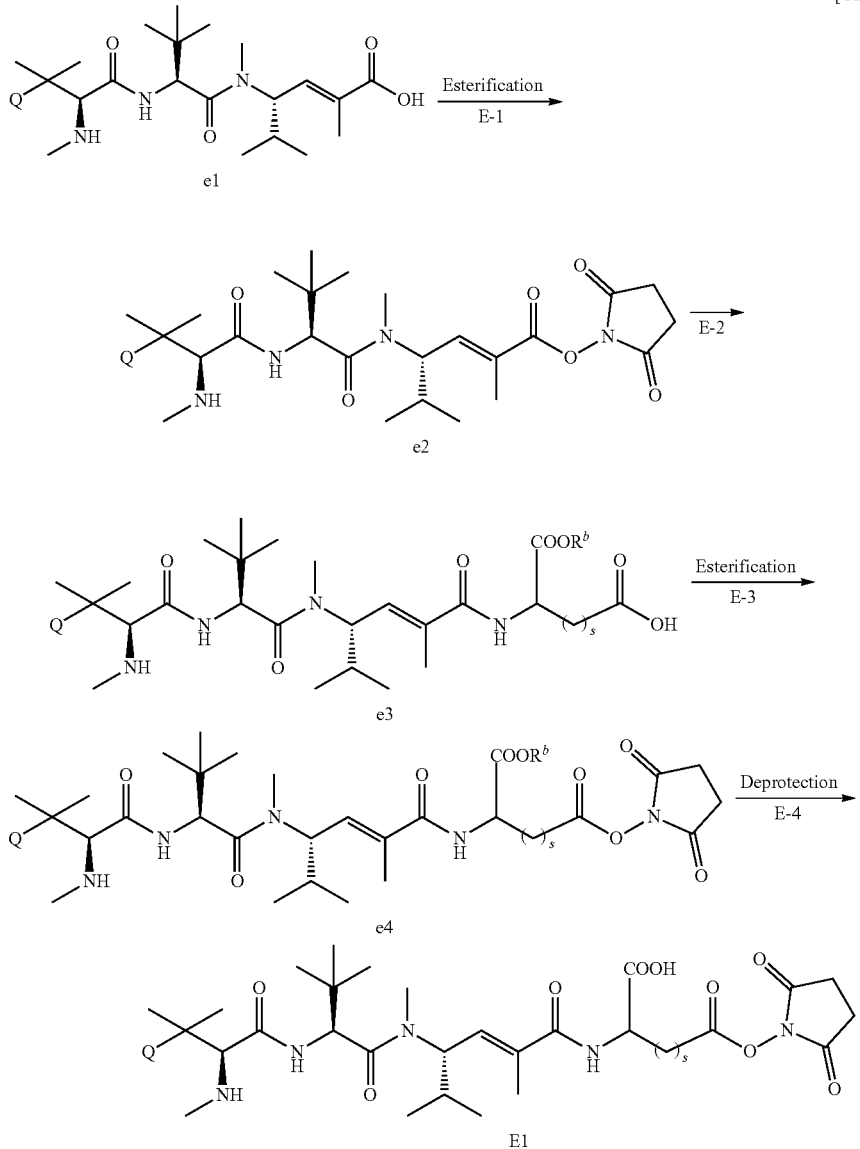

wherein, s represents 1 or 2; and $R^b$ is as defined above.

Compound e1 may be, for example, purchased as a commercial product.

[E-1 Step]

Compound e2 may be produced from compound e1 in accordance with the method described in the above A-15 step.

[E-2 Step]

Compound e3 may be produced from compound e2 in accordance with the method described in the above A-16 step.

[E-3 Step]

Compound e4 may be produced from compound e3 in accordance with the method described in the above A-17 step.

[E-4 Step]

Compound E1 may be produced from compound e4 in accordance with the method described in the above A-18 step.

Production Method F

When Z is a group represented by formula (Z-1); W is a group represented by formula (W-1); and $R^1$ is a hydrogen atom, the compound represented by formula (1) may be produced by, for example, the following production method:

[Chemical Formula 19]

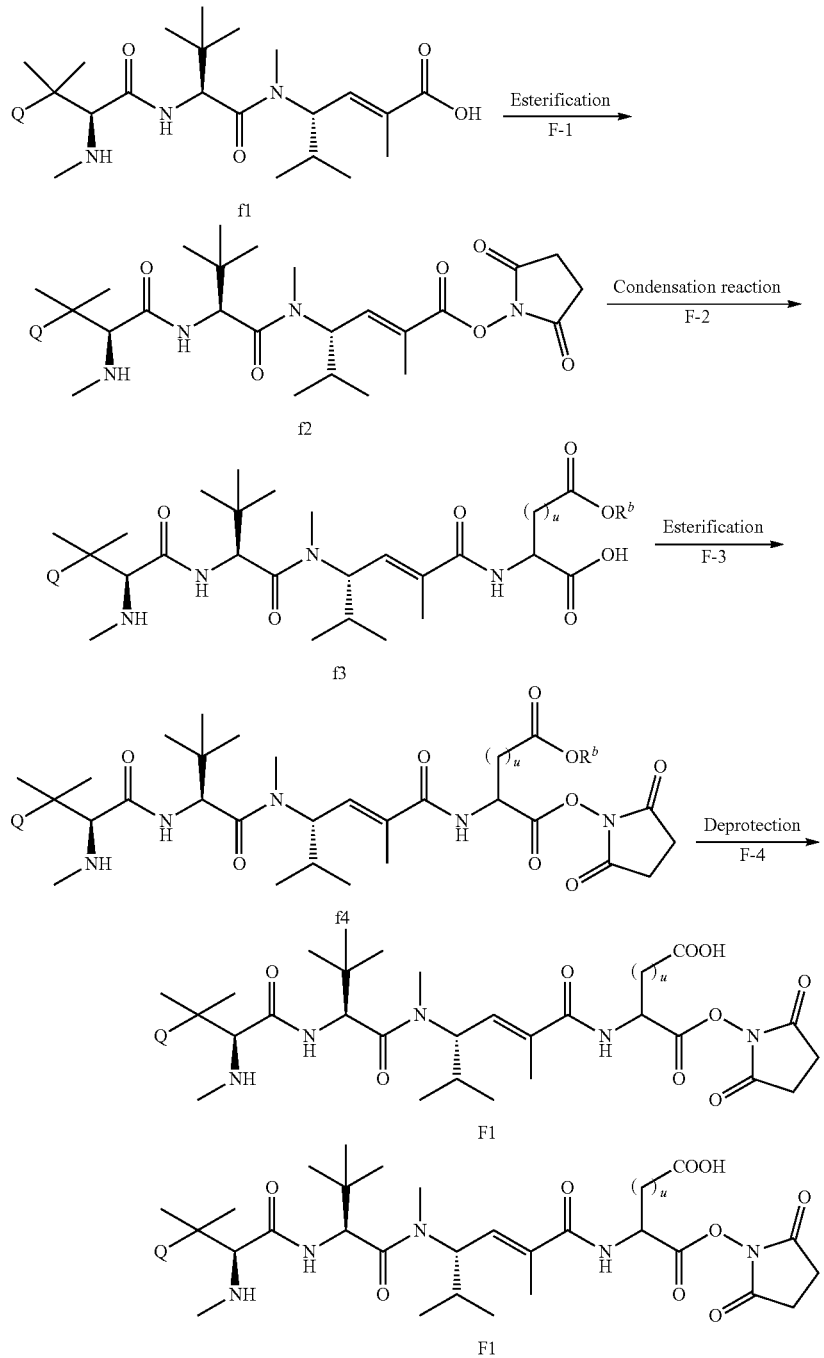

wherein, u is as defined in item 1; and $R^b$ is as defined above.

Compound f1 may be, for example, purchased as a commercial product.

[F-1 Step]

Compound f2 may be produced from compound f1 in accordance with the method described in the above A-15 step.

[F-2 Step]

Compound f3 may be produced from compound f2 in accordance with the method described in the above A-16 step.

[F-3 Step]

Compound f4 may be produced from compound f3 in accordance with the method described in the above A-17 step.

[F-4 Step]

Compound F1 may be produced from compound f4 in accordance with the method described in the above A-18 step.

The antibody-drug conjugate of the present invention represented by formula (2) may be produced by, for example, the following production method D:

Production Method D

[Chemical Formula 20]

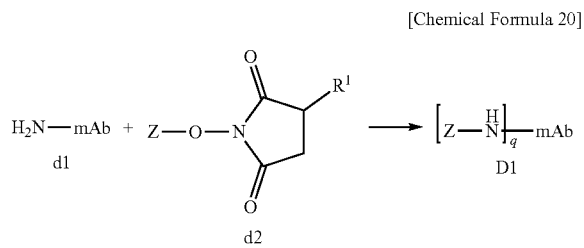

wherein, mAb, q, $R^1$ and Z are as defined in item 1 and item 4.

[D-1 Step]

Compound D1 may be produced by reacting compound d1 and compound d2 in an appropriate buffer solution. This step may be carried out in accordance with the method described in Antibody-Drug Conjugates (edited by Laurent Ducry, published by Humana Press, 2013) and the like.

The drug antibody ratio q or average antibody drug ratio of compound D1 obtained may be analyzed in accordance with the method described in Antibody-Drug Conjugates (edited by Laurent Ducry, published by Humana Press, 2013) and the like.

The production methods for the hemiasterlin derivative and antibody-drug conjugate according to the present invention have been shown in the above. However, the hemiasterlin derivative and antibody-drug conjugate according to the present invention may also be produced even by a method other than those, for example, by appropriately combining methods known to a person having ordinary skill in the art.

Appropriate bases used in each step of the above production methods should be selected as appropriate depending on reactions, types of raw material compounds and the like, and examples thereof include alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium t-butoxide; organometallic bases such as butyllithium and lithium diisopropylamide; and organic bases such as triethylamine, diisopropylethylamine, pyridine, 4-dimethylaminopyridine (DMAP) and 1,8-diazabicyclo[5.4.0]-7-undecene (DBU).

Appropriate solvents used in each step of the above production methods should be selected as appropriate depending on reactions, types of raw material compounds and the like, and examples thereof include alcohols such as methanol, ethanol and isopropanol; ketones such as acetone and methyl ketone; halogenated hydrocarbons such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethylsulfoxide (DMSO); nitriles such as acetonitrile; distilled water; and the like, and one of these solvents may be used singly, or two or more of them may be mixed for use. In addition, depending on the type of reactions, organic bases such as triethylamine, diisopropylethylamine and pyridine may be used as the solvent.

The hemiasterlin derivative and antibody-drug conjugate according to the present invention may be separated and purified by methods known to a person having ordinary skill in the art. Examples thereof include extraction, partitioning, reprecipitation, column chromatography (for example, silica gel column chromatography, ion exchange column chromatography or preparative liquid chromatography) or recrystallization.

As the recrystallization solvent, for example, alcohol solvents such as methanol, ethanol and 2-propanol; ether solvents such as diethyl ether; ester solvents such as ethyl acetate; aromatic hydrocarbon solvents such as benzene and toluene; ketone solvents such as acetone; halogenated solvents such as dichloromethane and chloroform; hydrocarbon solvents such as hexane; aprotic solvents such as dimethylformamide acetonitrile; water; or mixed solvents thereof may be used.

As other purification method, the method described in The Experimental Chemistry (edited by The Chemical Society of Japan, Maruzen), vol. 1 and the like may be used. In addition, determination of the molecular structure of the hemiasterlin derivative and antibody-drug conjugate according to the present invention may be readily carried out by spectroscopic approaches such as nuclear magnetic resonance, infrared absorption technique and circular dichroism spectroscopy, or mass spectrometry, with reference to the structure derived from their respective raw material compounds.

In addition, intermediates or final products in the above production methods may also be derivatized into other compounds included in the present invention by converting their functional groups as appropriate, in particular, by extending various side chains using an amino group, hydroxy group, carbonyl group, halogen atom or the like as the basis, and upon this, by carrying out protection and deprotection of the above functional groups as necessary. The conversion of functional groups and extension of side chains may be carried out by general methods that are conventionally performed (for example, see Comprehensive Organic Transformations, R. C. Larock, John Wiley & Sons Inc. (1999) and the like).

The hemiasterlin derivative and antibody-drug conjugate according to the present invention may have asymmetry or may have a substituent having an asymmetric carbon, and optical isomers are present in such compounds. Optical isomers may be produced in accordance with conventional methods. Examples of the production method include a method of using a raw material having an asymmetric point or a method of introducing asymmetry in the midway stage. For example, in the case of optical isomers, optical isomers may be obtained by using optically active raw materials or by carrying out optical resolution or the like at an appropriate stage during the production process. When the hemiasterlin derivative according to the present invention has a basic functional group, examples of the optical resolution method include a diastereomer method, in which a salt is formed using an optically active acid (for example, monocarboxylic acids such as mandelic acid, N-benzyloxyalanine and lactic acid; dicarboxylic acids such as tartaric acid, o-diisopropylidene tartaric acid and malic acid; sulfonic acids such as camphorsulfonic acid and bromocamphorsulfonic acid) in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents).

When the hemiasterlin derivative or synthetic intermediate thereof according to the present invention has an acidic functional group such as a carboxyl group, optical resolution can also be carried out by using an optically active amine (for example, an organic amine such as 1-phenylethylamine, quinine, quinidine, cinchonidine, cinchonine and strychnine) to form a salt.

Examples of the temperature at which the salt is formed include the range from −50° C. to the boiling point of the solvent, preferably include the range from 0° C. to the boiling point, and more preferably include the range from room temperature to the boiling point of the solvent. In order to improve optical purity, it is desirable that the temperature be once raised to the vicinity of the boiling point of the solvent. Upon separating the precipitated salt by filtration, the yield may be improved by cooling as necessary. Examples of the amount of the optically active acid or amine to be used include the range of about 0.5 to about 2.0 equivalent to the substrate, and preferably include the range around 1 equivalent. As necessary, an optically active salt with high purity can be obtained by recrystallizing a crystal in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). In addition, a free form may be obtained by treating a salt that has been optically resolved with an acid or base through a conventional method, as necessary.

Among the raw materials or intermediates in the production methods described above, those, for which the production method was not described, are either commercially available compounds or may be synthesized from commercially available compounds by methods known to a person having ordinary skill in the art or methods equivalent thereto.

The antibody-drug conjugate according to the present invention, and a pharmaceutical composition containing it are useful as an anticancer agent (for example, a therapeutic drug for breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma, leukemia and the like).

The antibody-drug conjugate according to the present invention may be administered through oral administration or parenteral administration, directly or as a formulation using an appropriate dosage form. Examples of the dosage form include, but are not limited to, liquid, suspension and injection. These formulations are produced by known methods, using a pharmaceutically acceptable additive.

For the additive, excipients, disintegrating agents, binders, glidants, lubricants, coating agents, solubilizing agents, solubilization aids, thickening agents, dispersing agents, stabilizers, sweetening agents, perfumes and the like may be used depending on purposes. Specifically, examples thereof include lactose, mannitol, crystalline cellulose, low substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide and talc.

Examples of an "anticancer compound" that may be used in combination with or combined with the antibody-drug conjugate according to the present invention include at least one or more antitumor agents selected from the group consisting of anticancer alkylating agents, anticancer antimetabolites, anticancer antibiotics, anticancer platinum coordination compounds, anticancer camptothecin derivatives, anticancer tyrosine kinase inhibitors, anticancer serine-threonine kinase inhibitors, anticancer phospholipid kinase inhibitors, anticancer monoclonal antibodies, interferons, biological response modifiers, hormonal agents, immune checkpoint inhibitors, epigenetics-related molecule inhibitors, post-translational protein modification inhibitors and other antitumor agents. Specific examples of the "anticancer compound" that may be used in combination with or combined with the antibody-drug conjugate according to the present invention include azacitidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans-retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, trastuzumab emtansine, gemtuzumab ozogamicin and inotuzumab ozogamicin.

From the above, the antibody-drug conjugate according to the present invention and a pharmaceutical composition comprising the same may be used for treatment of cancer. That is, it can also be said that one aspect of the present invention is a method of treating cancer, comprising administering the antibody-drug conjugate or a pharmaceutical composition comprising the same to a subject suffering from cancer. The subject suffering from cancer may be a human patient or animals other than human.

EXAMPLES

Hereinafter, the present invention will be explained further specifically with reference to Reference Examples, Examples and Test Examples, but the present invention is not limited to them, of course. Note that the names of compounds shown in the following Reference Examples and Examples do not necessarily follow the IUPAC nomenclature of chemistry.

Compounds of Reference Examples and Examples may be obtained as an acid addition salt such as a TFA salt, depending on a method of treatment after the reaction and the like.

In order to simplify description of the specification, abbreviations as shown below may be used in Reference Examples, Examples and the tables in Examples. As abbreviations used for substituents, Me represents a methyl group, Et represents an ethyl group, Boc represents a tert-butoxycarbonyl group and Ph represents a phenyl group. TFA represents trifluoroacetic acid, THF represents tetrahydrofuran, DMSO represents dimethyl sulfoxide, HEPES represents 2-[4-(2-hydroxyethyl)piperazin-1-yl]ethanesulfonic acid and EDTA represents ethylenediaminetetraacetic acid. For symbols used for NMR, s means a singlet, d means a doublet, dd means a doublet of doublets, t means a triplet, q means a quartet, m means a multiplet, br means broad, brs means a broad singlet, brd means a broad doublet, brm means a broad multiplet, and J means the binding constant.

High Performance Liquid Chromatography-Mass Spectrometer; measurement conditions for LCMS are as follows, and the observed value of mass spectrometry [MS (m/z)] is shown as $[M+nH]^{n+}/n$, $[M+Na]^+$ or $[M-nH]^{n-}/n$, and the retention time is shown as Rt (min). Note that, for each found value, the measurement conditions used for the measurement are denoted by A to D or F to H.

Measurement Condition A
  Detection Equipment: Shimadzu LCMS-IT-TOF
  Column: Phenomenex Kinetex (1.7 μm C18, 50 mm×2.10 mm)
  Solvents: solution A: 0.1% HCOOH/CH$_3$CN, solution B: 0.1% HCOOH/H$_2$O
  Gradient Condition:
    0.0 min; A/B=1:99
    0.0 to 1.4 min; Linear gradient from 1% to 95% A
    1.4 to 1.6 min; A/B=95:5
    1.6 to 2.0 min; A/B=1:99
  Flow Rate: 1.2 mL/min
  UV: 220/254 nm
  Column Temperature: 40° C.

Measurement Condition B
  Detection Equipment: Shimadzu LCMS-IT-TOF
  Column: Phenomenex Kinetex (1.7 μm C18, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.4 min; Linear gradient from 10% to 90% A
    1.4 to 1.6 min; A/B=90:10
    1.6 to 2.0 min; A/B=10:90
  Flow Rate: 1.2 mL/min
  UV: 220/254 nm
  Column Temperature: 40° C.

Measurement Condition C
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=1:99
    0.0 to 1.4 min; Linear gradient from 1% to 95% A
    1.4 to 1.6 min; A/B=95:5
    1.6 to 2.0 min; A/B=1:99
  Flow Rate: 1.2 mL/min
  UV: 220/254 nm
  Column Temperature: 40° C.

Measurement Condition D
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.4 min; Linear gradient from 10% to 95% A
    1.4 to 1.6 min; A/B=95:5
    1.6 to 2.0 min; A/B=10:90
  Flow Rate: 1.2 mL/min
  UV: 220/254 nm
  Column Temperature: 40° C.

Measurement Condition E
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.4 min; Linear gradient from 10% to 90% A
    1.4 to 1.6 min; A/B=90:10
    1.6 to 2.0 min; A/B=10:90
  Flow Rate: 1.2 mL/min
  UV: 220/254 nm
  Column Temperature: 40° C.

Measurement Condition G
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=100:0
    0.0 to 1.6 min; Linear gradient from 100% to 1% A
    1.6 to 2.0 min; A/B=1:99
  Flow Rate: 1.2 mL/min
  UV: 220/254 nm
  Column Temperature: 40° C.

Measurement Condition H
  Detection Equipment: Shimadzu LCMS-2020
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.7 min; Linear gradient from 10% to 99% A
    1.7 to 1.9 min; A/B=99:1
    1.9 to 3.0 min; A/B=10:90
  Flow Rate: 0.5 mL/min
  UV: 220/254 nm
  Column Temperature: 40° C.

High Performance Liquid Chromatography; measurement conditions for determining the average drug antibody ratio (average DAR) are as follows.

As a pretreatment for measurement to determine the average drug antibody ratio (average DAR), deglycosidation reaction was carried out by adding PNGase to an antibody-drug conjugate obtained. The present condition may be achieved in accordance with the method described in Antibody-Drug Conjugates (edited by Laurent Ducry, published by Humana Press, 2013) and the like.

Measurement Condition F
  Mass Spectrometer: Synapt HDMS (Waters Corporation)
  Liquid Chromatography: Acquity M class (Waters Corporation)
  Column: Intrada WP—RP (catalog No. WPR22, 50 mm×2 mm, Imtakt Corporation)

Solvents: solution A: 0.1% HCOOH/0.025% TFA/CH₃CN, solution B: 0.1% HCOOH/0.025% TFA/H₂O Gradient Condition:
 0.0 to 1.0 min; A/B=5:95
 1.0 to 9.0 min; Linear gradient from 5% to 60% A
 9.0 to 12.0 min; A/B=60:40
 12.0 to 15.0 min; A/B=5:95

Flow Rate: 0.1 mL/min
Column Temperature: 37° C.

Reference Example 1

N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N,3-dimethyl-L-valinamide

[Chemical Formula 21]

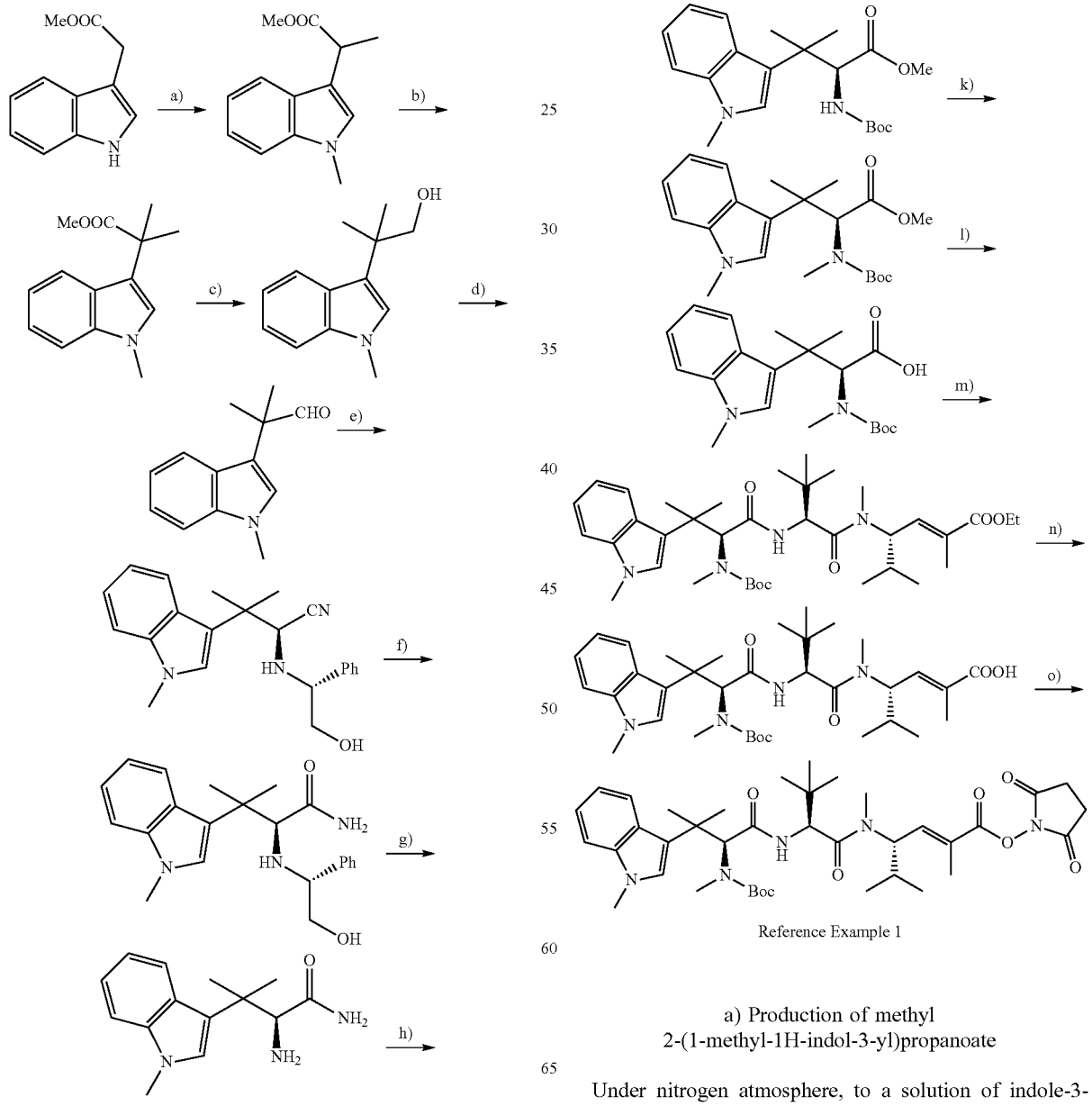

Reference Example 1 a) Production of methyl 2-(1-methyl-1H-indol-3-yl)propanoate

Under nitrogen atmosphere, to a solution of indole-3-acetic acid methyl ester (3.8 g) in tetrahydrofuran (87 mL)

at −78° C., potassium hexamethyldisilazide (1 mol/L tetrahydrofuran solution, 65.5 mL) was added dropwise, and the resultant mixture was then stirred at 0° C. for 2 hours. After cooling the reaction solution to −78° C., methyl iodide (23 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give methyl 2-(1-methyl-1H-indol-3-yl)propanoate (3.95 g).

$^1$H-NMR (400 MHz, CDCl$_3$):1.60 (3H, d, J=7.1 Hz), 3.67 (3H, s), 3.76 (3H, s), 4.02 (1H, q, J=7.1 Hz), 7.00 (1H, s), 7.12 (1H, t, J=7.8 Hz), 7.23 (1H, t, J=7.8 Hz), 7.29 (1H, d, J=7.8 Hz), 7.66 (1H, d, J=7.8 Hz).

b) Production of Methyl
2-methyl-2-(1-methyl-1H-indol-3-yl)propanoate

Under nitrogen atmosphere, to a solution of methyl 2-(1-methyl-1H-indol-3-yl)propanoate (3.94 g) in tetrahydrofuran (200 mL) at −78° C., potassium hexamethyldisilazide (1 mol/L tetrahydrofuran solution, 27.7 mL) was added dropwise, and the resultant mixture was then stirred at 0° C. for 2 hours. After cooling the reaction solution to −78° C., methyl iodide (15.4 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give methyl 2-methyl-2-(1-methyl-1H-indol-3-yl)propanoate (3.59 g).

$^1$H-NMR (400 MHz, CDCl$_3$):1.66 (6H, s), 3.61 (3H, s), 3.73 (3H, s), 6.91 (1H, s), 7.06 (1H, t, J=8.0 Hz), 7.19 (1H, t, J=8.0 Hz), 7.27 (1H, d, J=8.0 Hz), 7.61 (1H, d, J=7.9 Hz).

c) Production of 2-methyl-2-(1-methyl-1H-indol-3-yl)propan-1-ol

Under nitrogen atmosphere, to a solution of methyl 2-methyl-2-(1-methyl-1H-indol-3-yl)propanoate (3.59 g) in diethyl ether (169 mL) and dichloromethane (47 mL) at −78° C., diisobutylaluminum hydride (1 mol/L n-hexane solution, 38.8 mL) was added dropwise, and the resultant mixture was then stirred at 0° C. for 1 hour. After the reaction ended, water was added, and then, to the reaction mixture at 25° C., a saturated aqueous solution of potassium sodium tartrate was added, and the resultant mixture was then extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give 2-methyl-2-(1-methyl-1H-indol-3-yl)propan-1-ol (3.14 g).

$^1$H-NMR (400 MHz, CDCl$_3$):1.42 (6H, s), 3.74 (3H, s), 3.77 (2H, s), 6.87 (1H, s), 7.07 (1H, t, J=7.9 Hz), 7.20 (1H, t, J=7.9 Hz), 7.29 (1H, d, J=8.0 Hz), 7.75 (1H, d, J=8.0 Hz).

d) Production of 2-methyl-2-(1-methyl-1H-indol-3-yl)propanal

Under nitrogen atmosphere, a mixed solution of 2-methyl-2-(1-methyl-1H-indol-3-yl)propan-1-ol (3.14 g), tetrapropylammonium perruthenate (271 mg), N-methyl-morpholine-N-oxide (3.26 g) and molecular sieve 4A (7.7 g) in dichloromethane (110 mL) was stirred at 25° C. for 1 hour. After the reaction ended, the reaction solution was filtered through celite and the solvent was then distilled off, and the residue was purified by silica gel column chromatography (eluting solvent; hexane:ethyl acetate) to give 2-methyl-2-(1-methyl-1H-indol-3-yl)propanal (2.4 g).

$^1$H-NMR (400 MHz, CDCl$_3$):1.53 (6H, s), 3.77 (3H, s), 6.94 (1H, s), 7.07 (1H, t, J=8.0 Hz), 7.22 (1H, t, J=8.0 Hz), 7.30 (1H, d, J=8.0 Hz), 7.53 (1H, d, J=8.0 Hz), 9.47 (1H, s).

e) Production of (2S)-2-{[(1R)-2-hydroxy-1-phenyl-ethyl]amino}-3-methyl-3-(1-methyl-1H-indol-3-yl)butanenitrile Under nitrogen atmosphere, a solution of 2-methyl-2-(1-methyl-1H-indol-3-yl)propanal (2.4 g) and (R)-(−)-2-phenylglycinol (1.63 g) in toluene (47 mL) was subjected to heating reflux for 1.5 hours, and after distilling off water with a Dean-Stark apparatus, the solvent was distilled off. Under nitrogen atmosphere, dichloromethane (69 mL) at 0° C. was added to the residue and trimethylsilyl cyanide (2.36 g) was then added, and the resultant mixture was stirred at 25° C. for 96 hours. To the reaction solution, tetra-n-butylammonium fluoride (1 mol/L tetrahydrofuran solution, 1 mL) was added, and after stirring the solution for further 30 minutes, water was added and the resultant mixture was extracted with chloroform. The organic layer was dried over anhydrous sodium sulfate, and the solvent was distilled off under reduced pressure. The residue was purified by silica gel column chromatography (eluting solvent; hexane:ethyl acetate) to give (2S)-2-{[(1R)-2-hydroxy-1-phenylethyl] amino}-3-methyl-3-(1-methyl-1H-indol-3-yl)butanenitrile (2.74 g).

$^1$H-NMR (400 MHz, CDCl$_3$):1.64 (3H, s), 1.65 (3H, s), 3.49-3.55 (1H, m), 3.73 (1H, dd, J=10.9, 4.2 Hz), 3.79 (1H, s), 3.80 (3H, s), 4.05 (1H, dd, J=7.9, 3.6 Hz), 6.96-7.00 (2H, m), 7.11 (2H, d, J=8.0 Hz), 7.21-7.40 (6H, m).

f) Production of Nα-[(1R)-2-hydroxy-1-phenyl-ethyl]-β,β,1-trimethyl-L-tryptophanamide To a suspension of (2S)-2-{[(1R)-2-hydroxy-1-phenyl-ethyl]amino}-3-methyl-3-(1-methyl-1H-indol-3-yl)butanenitrile (2.74 g), dimethyl sulfoxide (6.16 g) and potassium carbonate (10.9 g) in methanol (50 mL) and water (2.1 mL), a 30% aqueous hydrogen peroxide solution (8.94 mL) was added at 0° C., and the resultant mixture was stirred at 45° C. for 1.5 hours. After the reaction ended, a saturated aqueous sodium thiosulfate solution was added, and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform: methanol) to give Nα-[(1R)-2-hydroxy-1-phenylethyl]-β,β, 1-trimethyl-L-tryptophanamide (2.32 g).

$^1$H-NMR (400 MHz, CDCl$_3$):1.49 (3H, s), 1.51 (3H, s), 2.06-2.14 (1H, br), 2.37 (1H, dd, J=6.0, 6.0 Hz), 3.44-3.50 (1H, m), 3.50-3.54 (1H, m), 3.56-3.63 (m, 2H), 3.75 (3H, s), 5.52 (1H, brs), 6.14 (1H, brs), 6.71-6.73 (2H, m), 6.81-6.85 (2H, m), 6.97-7.00 (2H, m), 7.10-7.18 (2H, m), 7.24-7.28 (2H, m).

g) Production of β,β,1-trimethyl-L-tryptophanamide

To a solution of Nα-[(1R)-2-hydroxy-1-phenylethyl]-β,β, 1-trimethyl-L-tryptophanamide (2.32 g) in methanol (65 mL), palladium hydroxide/carbon (2.8 g) was added, and the resultant mixture was stirred at room temperature for 3 hours under hydrogen atmosphere. The reaction solution was filtered through celite and the solvent was then distilled off, and the residue was purified by silica gel column chromatography (eluting solvent; chloroform: methanol) to give β,β,1-trimethyl-L-tryptophanamide (1.27 g).

$^1$H-NMR (400 MHz, DMSO-d6):1.24 (2H, brs), 1.28 (3H, s), 1.42 (3H, s), 3.68 (1H, s), 3.71 (3H, s), 6.93-7.00 (2H, m), 7.06 (1H, s), 7.11 (1H, t, J=7.7 Hz), 7.29 (1H, brs), 7.36 (1H, d, J=8.3 Hz), 7.88 (1H, d, J=8.2 Hz).

h) Production of Nα-(tert-butoxycarbonyl)-β,β,1-trimethyl-L-tryptophanamide

A mixed solution of β,β,1-trimethyl-L-tryptophanamide (1.27 g), sodium bicarbonate (522 mg), di-tert-butyl dicarbonate (1.35 g), tetrahydrofuran (13 mL), chloroform (13 mL) and water (6.5 mL) was stirred at 25° C. for 16 hours. After the reaction ended, water was added and the resultant mixture was extracted with chloroform. The organic layer was dried over anhydrous sodium sulfate, and the solvent was distilled off under reduced pressure. The residue was purified by silica gel column chromatography (eluting solvent; chloroform:methanol) to give Nα-(tert-butoxycarbonyl)-β,β,1-trimethyl-L-tryptophanamide (1.80 g).

$^1$H-NMR (400 MHz, CDCl$_3$):1.33 (3H, s), 1.47 (9H, s), 1.50 (3H, s), 3.73 (3H, d, J=1.3 Hz), 4.51 (1H, brs), 4.86 (1H, brs), 5.02 (1H, brd, J=8.2 Hz), 5.59 (1H, brd, J=6.4 Hz), 6.83 (1H, d, J=1.8 Hz), 7.15 (1H, t, J=7.3 Hz), 7.21-7.25 (1H, m), 7.30 (1H, d, J=8.2 Hz), 8.05 (1H, brd, J=7.3 Hz).

LC-MS: 346 (M+H)$^+$ (1.211 min, Measurement Condition A)

i) Production of N,N,Nα-tris(tert-butoxycarbonyl)-β,β,1-trimethyl-L-tryptophanamide A mixed solution of Nα-(tert-butoxycarbonyl)-β,β,1-trimethyl-L-tryptophanamide (1.79 g), di-tert-butyl dicarbonate (2.8 g), N,N-diisopropylethylamine (2.68 g), 4-dimethylaminopyridine (0.19 g) and chloroform (20 mL) was stirred at 25° C. for 2.5 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give N,N,Nα-tris(tert-butoxycarbonyl)-β,β,1-trimethyl-L-tryptophanamide (1.99 g).

$^1$H-NMR (400 MHz, CDCl$_3$):1.08-1.58 (33H, m), 3.70 (3H, s), 4.67-4.90 (0.2H, m), 5.25-5.45 (0.8H, m), 6.00-6.03 (1H, m), 6.81-6.87 (1H, m), 7.04-7.09 (1H, m), 7.13-7.18 (1H, m), 7.21-7.27 (1H, m), 7.91-7.94 (1H, m).

LC-MS: 546 (M+H)$^+$ (1.630 min, Measurement Condition A)

j) Production of methyl N-(tert-butoxycarbonyl)-β,β,1-trimethyl-L-tryptophanate

Under nitrogen atmosphere, to a solution of N,N,Nα-tris(tert-butoxycarbonyl)-β,β,1-trimethyl-L-tryptophanamide (2.29 g) in methanol (21 mL), lithium methoxide (176 mg) was added at 0° C., and the resultant mixture was then stirred at 25° C. for 2 hours. After the reaction ended, a saturated aqueous ammonium chloride solution was added, and the reaction mixture was extracted with ethyl acetate. The organic layer was washed with saturated brine and then dried over anhydrous sodium sulfate, and the solvent was distilled off under reduced pressure. The residue was purified by silica gel column chromatography (eluting solvent; hexane:ethyl acetate) to give methyl N-(tert-butoxycarbonyl)-β,β,1-trimethyl-L-tryptophanate (927 mg).

$^1$H-NMR (400 MHz, CDCl$_3$):1.17-1.59 (15H, m), 3.45 and 3.58 (3H, 2brs), 3.71 (3H, s), 4.56-4.73 (1.2H, m), 5.06 (0.8H, brd, J=7.3 Hz), 6.81-6.82 (1H, m), 7.05-7.10 (1H, m), 7.16-7.21 (1H, m), 7.24-7.29 (1H, m), 7.73-7.80 (1H, m).

LC-MS: 361 (M+H)$^+$ (1.379 min, Measurement Condition A).

k) Production of methyl N-(tert-butoxycarbonyl)-N,β,β,1-tetramethyl-L-tryptophanate Under nitrogen atmosphere, to a solution of methyl N-(tert-butoxycarbonyl)-β,β,1-trimethyl-L-tryptophanate (927 mg) in N,N-dimethylformamide (13 mL), sodium hydride 60% dispersion (168 mg) was added at 0° C., and the resultant mixture was then stirred at 25° C. for 15 minutes. After cooling the reaction suspension to 0° C., methyl iodide (1.1 g) was added thereto, and the reaction solution was then stirred at 25° C. for 1 hour. After the reaction ended, water was added and the resultant mixture was extracted with ethyl acetate. The organic layer was dried over anhydrous sodium sulfate, and the solvent was distilled off under reduced pressure. The residue was purified by silica gel column chromatography (eluting solvent; hexane:ethyl acetate) to give methyl N-(tert-butoxycarbonyl)-N,β,β,1-tetramethyl-L-tryptophanate (915 mg).

$^1$H-NMR (400 MHz, CDCl$_3$):1.42 (9H, s), 1.52 and 1.64 (6H, 2s), 2.80 and 2.86 (3H, 2s), 3.46 (3H, s), 3.71 (3H, s), 5.27 and 5.52 (1H, 2s), 6.85 (1H, s), 7.07-7.27 (3H, m), 7.78 and 7.92 (1H, 2d, J=7.88 Hz).

LC-MS: 397 (M+Na)+(1.406 min, Measurement Condition B)

l) Production of N-(tert-butoxycarbonyl)-N,β,β,1-tetramethyl-L-tryptophan

To a solution of methyl N-(tert-butoxycarbonyl)-N,β,β,1-tetramethyl-L-tryptophanate (639 mg) in water (11 mL)-methanol (44 mL), 1 mol/L lithium hydroxide (13.5 mL) was added, and the resultant mixture was stirred at 60° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform: methanol) to give N-(tert-butoxycarbonyl)-N,β,β,1-tetramethyl-L-tryptophan (610 mg).

$^1$H-NMR (400 MHz, CDCl$_3$):1.43 (9H, s), 1.53 (3H, s), 1.63 (3H, s), 2.76 and 2.89 (3H, 2s), 3.71 (3H, s), 5.36 and 5.44 (1H, 2s), 6.85 and 6.87 (1H, 2s), 7.02-7.11 (1H, m), 7.18 (1H, t, J=7.3 Hz), 7.24-7.27 (1H, m), 7.81 and 7.96 (1H, 2d, J=7.9 Hz).

LC-MS: 361 (M+H)$^+$, 359 (M−H)$^−$ (1.300 min, Measurement Condition A).

m) Production of N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide A mixed solution of N-(tert-butoxycarbonyl)-N,β,β,1-tetramethyl-L-tryptophan (500 mg), ethyl (2E,4S)-2,5-dimethyl-4-[methyl(3-methyl-L-valyl)amino]hex-2-enoate (520 mg), 1-ethyl-3-(3-dimethylaminopropyl)carbodiimide hydrochloride (399 mg), 1-hydroxy-1H-benzotriazole monohydrate (425 mg) and N,N-dimethylformamide (5 mL) was stirred at 25° C. for 16 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide (759 mg).

LC-MS: 655 (M+H)+ (1.714 min, Measurement Condition A)

n) Production of N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide To a solution of N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide (127 mg) in water (1.55 mL)-methanol (4.65 mL), 1 mol/L lithium hydroxide (1.65 mL) was added, and the resultant mixture was stirred at 25° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform:methanol) to give N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide (93 mg).

LC-MS: 627 (M+H)+(1.508 min, Measurement Condition A)

o) Production of N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N, 3-dimethyl-L-valinamide (Reference Example 1)

A mixed solution of N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide (185 mg), N-hydroxysuccinimide (97 mg), bromotripyrrolidinophosphonium hexafluorophosphate (391 mg), 4-dimethylaminopyridine (102 mg), N,N-diisopropylethylamine (108 mg) and N,N-dimethylformamide (2.8 mL) was stirred at 25° C. for 4 hours. After the reaction ended, water was added and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N, 3-dimethyl-L-valinamide (166 mg).

$^1$H-NMR (400 MHz, CDCl$_3$):8.27 and 7.96 (1H, 2d, J=7.9 Hz), 7.16-7.04 (4H, m), 6.88 (1H, d, J=9.1 Hz), 6.17 and 6.09 (1H, 2d, J=8.5 Hz), 5.96 and 5.66 (1H, 2s), 5.07 (1H, t, J=9.3 Hz), 4.45 and 3.87 (1H, 2d, J=8.6 Hz), 3.74 and 3.73 (3H, 2s), 2.99 (3H, s), 2.95 (3H, s), 2.83 (4H, brs), 1.97 (3H, s), 1.92-1.86 (1H, m), 1.57-1.42 (14H, m), 0.89 (3H, d, J=6.1 Hz), 0.83-0.80 (3H, m), 0.48 and 0.41 (9H, 2s).

LC-MS: 724 (M+H)+(1.573 min, Measurement Condition A)

Reference Example 2

N-(tert-Butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide

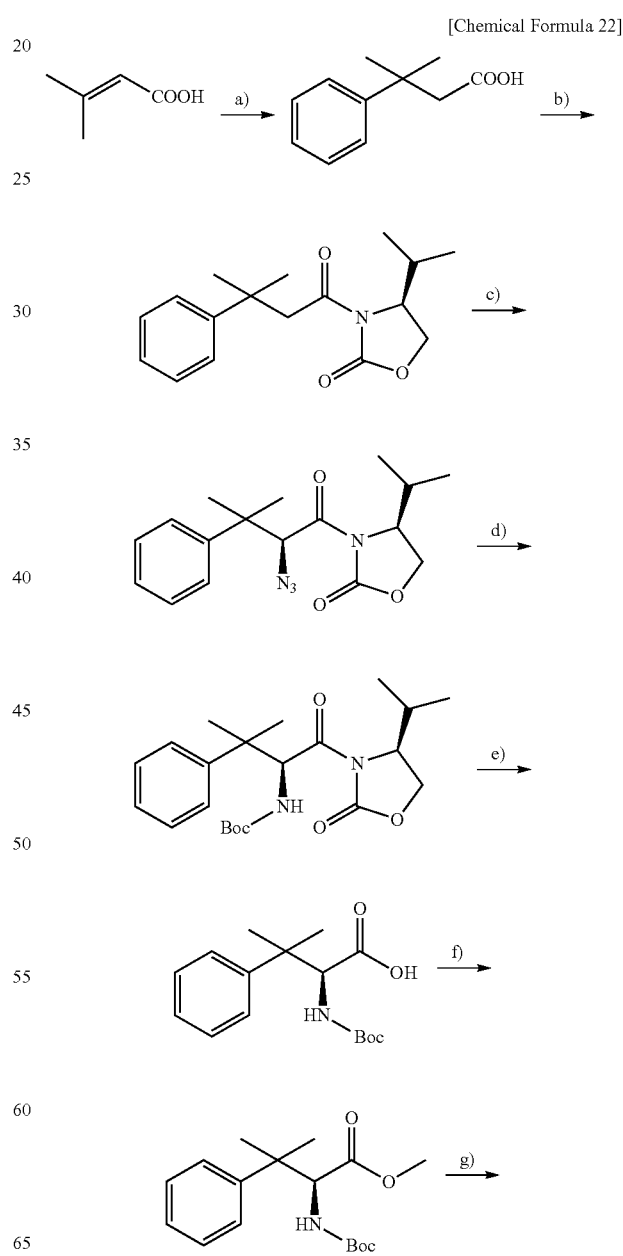

[Chemical Formula 22]

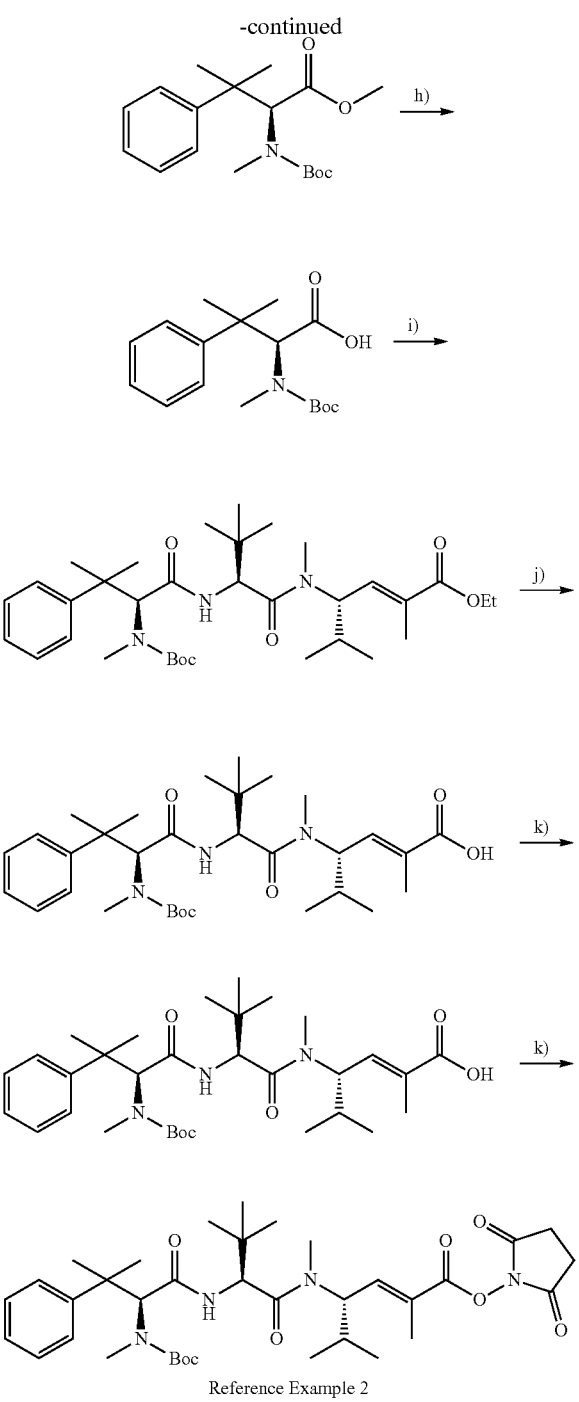

Reference Example 2 a) Production of 3-methyl-3-phenylbutanoic Acid

To a solution of 3-methyl-2-butenoic acid (15 g) in benzene (100 mL), aluminum chloride (24.1 g) was added at 10° C., and the resultant mixture was stirred for 30 minutes and then stirred at 40° C. for 1 hour. After cooling the reaction solution to 0° C., ice water was added, and the resultant mixture was extracted with tert-butyl methyl ether, concentrated to some extent, and the organic layer was extracted with a saturated aqueous sodium bicarbonate solution. The pH of the aqueous layer was changed to 2 with concentrated hydrochloric acid, and the resultant mixture was extracted with tert-butyl methyl ether. The organic layer was dried over anhydrous magnesium sulfate, and the solvent was distilled off under reduced pressure to give 3-methyl-3-phenylbutanoic acid (26.3 g).

$^1$H-NMR (400 MHz, CDCl$_3$):1.46 (6H, s), 2.65 (2H, s), 7.20 (1H, t, J=7.2 Hz), 7.31 (11H, t, J=7.2 Hz), 7.37 (2H, d, J=7.2 Hz).

b) Production of (4S)-3-(3-methyl-3-phenylbutanoyl)-4-(propan-2-yl)-1,3-oxazolidin-2-one To a solution of 3-methyl-3-phenylbutanoic acid (17.2 g) in THF (900 mL), triethylamine (23.7 mL) and pivaloyl chloride (15.3 mL) was added at −78° C. After raising the temperature to 0° C., the resultant mixture was stirred for 1 hour. Separately, to a solution of (S)-isopropyloxazolidinone (19.5 g) in THF (760 mL), n-butyllithium (1.64 mol/L hexane solution, 89.8 mL) was added at −78° C., the resultant mixture was stirred for 30 minutes to prepare a lithium salt. The previous reaction solution was cooled to −78° C., the lithium salt was added dropwise, the resultant mixture was stirred for 1 hour, and the temperature was then raised to 0° C. After stirring the mixture for further 30 minutes, water was added, and the resultant mixture was extracted with tert-butyl methyl ether. The organic layer was washed with saturated brine and dried over anhydrous magnesium sulfate. The solvent was distilled off under reduced pressure, and the residue was purified by silica gel column chromatography (eluting solvent; hexane:tert-butyl methyl ether) to give (4S)-3-(3-methyl-3-phenylbutanoyl)-4-(propan-2-yl)-1,3-oxazolidin-2-one (27.0 g).

$^1$H-NMR (400 MHz, CDCl$_3$):0.723 (3H, d, J=6.8 Hz), 0.80 (3H, d, J=6.8 Hz), 1.49 (s, 6H), 2.13-2.18 (m, 1H), 3.36 (s, 3H), 3.99-4.09 (m, 2H), 4.20-4.23 (m, 1H), 7.16-7.20 (m, 1H), 7.28-7.32 (m, 2H), 7.38-7.40 (m, 2H).

c) Production of (4S)-3-[(2S)-2-azido-3-methyl-3-phenylbutanoyl]-4-(propan-2-yl)-1,3-oxazolidin-2-one A suspension of (4S)-3-(3-methyl-3-phenylbutanoyl)-4-(propan-2-yl)-1,3-oxazolidin-2-one (27.0 g) in THF (560 mL) was cooled to −78° C., potassium hexamethyldisilazide (1.06 mol/L tetrahydrofuran solution, 99.5 mL) was added, and the resultant mixture was stirred for 1.5 hours. A solution of 2,4,6-triisopropylbenzenesulfonyl azide (40 g) in THF (330 mL) at −78° C. was added, and after 10 minutes, acetic acid (24.5 mL) was added, the temperature was raised to 40° C., and the resultant mixture was stirred for 1 hour. Saturated brine was added, and the resultant mixture was extracted with tert-butyl methyl ether. The organic layer was washed with a saturated aqueous sodium bicarbonate solution and saturated brine, and the organic layer was then dried over anhydrous magnesium sulfate. The solvent was distilled off under reduced pressure, and the residue was purified by silica gel column chromatography (eluting solvent; hexane:chloroform) to give (4S)-3-[(2S)-2-azido-3-methyl-3-phenylbutanoyl]-4-(propan-2-yl)-1,3-oxazolidin-2-one (16.4 g).

$^1$H-NMR (400 MHz, CDCl$_3$):0.80 (3H, d, J=6.8 Hz), 0.84 (3H, d, J=7.2 Hz), 1.54 (3H, s), 1.56 (3H, s), 2.28-2.33 (1H, m), 3.54-3.59 (1H, m), 3.87-3.90 (1H, m), 3.95-3.98 (1H, m), 5.66 (1H, s), 7.23-7.420 (5H, m).

d) Production of Tert-Butyl {(2S)-3-methyl-1-oxo-1-[(4S)-2-oxo-4-(propan-2-yl)-1,3-oxazolidin-3-yl]-3-phenylbutan-2-yl}carbamate To a solution of (4S)-3-[(2S)-2-azido-3-methyl-3-phenylbutanoyl]-4-(propan-2-yl)-1,3-oxazolidin-2-one (16.4 g) in ethyl acetate (1200 mL), di-tert-butyl dicarbonate (24.0 g) and 10% Pd—C(11.6 g, 50% wet) were added, and the resultant mixture was stirred for 2 hours under hydrogen atmosphere. The reaction solution was filtered through celite, and was washed with ethyl acetate. The solvent was distilled off under reduced pressure, and the residue was purified by silica gel column chromatography (eluting solvent; hexane:tert-butyl methyl ether) to give tert-butyl {(2S)-3-methyl-1-oxo-1-[(4S)-2-oxo-4-(propan-2-yl)-1,3-oxazolidin-3-yl]-3-phenylbutan-2-yl}carbamate (16.1 g).

$^1$H-NMR (400 MHz, CDCl$_3$):0.77 (3H, d, J=6.8 Hz), 0.82 (3H, d, J=6.8 Hz), 1.42 (3H, s), 1.43 (9H, s), 1.48 (3H, s), 2.20-2.29 (1H, m), 3.45 (1H, t, J=8.8 Hz), 3.80-3.83 (1H, m), 3.89-3.92 (1H, dd, J=2.0 Hz, J=8.4 Hz), 5.16 (1H, brs), 6.13 (1H, d, J=9.6 Hz), 7.21-7.26 (1H, m), 7.29-7.33 (2H, m), 7.42 (2H, d, J=7.2 Hz).

e) Production of N-(tert-butoxycarbonyl)-β,β-dimethyl-L-phenylalanine

To a solution of tert-butyl {(2S)-3-methyl-1-oxo-1-[(4S)-2-oxo-4-(propan-2-yl)-1,3-oxazolidin-3-yl]-3-phenylbutan-2-yl}carbamate (16.1 g) in THF (468 mL) and water (117 mL), a 30% aqueous hydrogen peroxide solution (32.5 mL) and an aqueous lithium hydroxide solution (1 mol/L, 119 mL) were added at 0° C., the temperature was raised to 25° C., and the resultant mixture was stirred for 3 hours. An aqueous sodium bisulfate solution (1.5 mol/L, 470 mL) was added at 0° C., the temperature was raised to 25° C., and the resultant mixture was stirred for 1 hour. The pH was changed to 3 with an aqueous citric acid solution (1 mol/L), and the resultant mixture was extracted with tert-butyl methyl ether. The organic layer was washed with saturated brine, and the organic layer was dried over anhydrous magnesium sulfate. The solvent was distilled off under reduced pressure to give N-(tert-butoxycarbonyl)-β,β-dimethyl-L-phenylalanine (14.2 g).

$^1$H-NMR (400 MHz, CDCl$_3$):1.38 (9H, s), 1.44 (3H, s), 1.46 (3H, s), 4.56 (1H, brd, J=11.6 Hz), 4.94 (1H, brd, J=14.4 Hz), 7.21-7.38 (5H, m).

f) Production of N-(tert-butoxycarbonyl)-β,β-dimethyl-L-phenylalanine methyl ester To a solution of N-(tert-butoxycarbonyl)-β,β-dimethyl-L-phenylalanine (14.2 g) in N,N-dimethylformamide (84 ml), sodium carbonate (8.44 g) and methyl iodide (9.91 mL) were added, and the resultant mixture was stirred at 25° C. for 15 hours. After cooling the mixture to 0° C., chilled water was added and the resultant mixture was extracted with tert-butyl methyl ether, and the organic layer thus obtained was washed with saturated brine and then dried over anhydrous magnesium sulfate. The solvent was distilled off under reduced pressure, and the residue was purified by silica gel column chromatography (eluting solvent; hexane:tert-butyl methyl ether) to give N-(tert-butoxycarbonyl)-β,β-dimethyl-L-phenylalanine methyl ester (11.1 g).

$^1$H-NMR (400 MHz, CDCl$_3$):1.36 (9H, s), 1.37 (3H, s), 1.41 (3H, s), 3.48 (3H, brs), 4.49 (1H, brd, J=9.8 Hz), 4.98 (1H, brd, J=9.1 Hz), 7.18-7.22 (1H, m), 7.27-7.33 (4H, m).

g) Production of N-(tert-butoxycarbonyl)-N,β,β-trimethyl-L-phenylalanine methyl ester By the same approach as Reference Example 1-k), from N-(tert-butoxycarbonyl)-β,β-dimethyl-L-phenylalanine methyl ester (307 mg), N-(tert-butoxycarbonyl)-N,β,β-trimethyl-L-phenylalanine methyl ester (245 mg) was obtained.

LC-MS: 344 (M+Na)$^+$ (1.589 min, Measurement Condition C)

h) Production of N-(tert-butoxycarbonyl)-N,β,β-trimethyl-L-phenylalanine

By the same approach as Reference Example 1-1), from N-(tert-butoxycarbonyl)-N,β,β-trimethyl-L-phenylalanine methyl ester (235 mg), N-(tert-butoxycarbonyl)-N,β,β-trimethyl-L-phenylalanine (195 mg) was obtained.

LC-MS: 330 (M+Na)$^+$ (1.420 min, Measurement Condition C)

i) Production of N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide By the same approach as Reference Example 1-m), from N-(tert-butoxycarbonyl)-N,β,β-trimethyl-L-phenylalanine (195 mg), N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide (307 mg) was obtained.

LC-MS: 624 (M+Na)$^+$ (1.797 min, Measurement Condition C)

j) Production of N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide By the same approach as Reference Example 1-n), from N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide (307 mg), N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide (286 mg) was obtained.

LC-MS: 596 (M+Na)$^+$, 572 (M–H)$^-$ (1.596 min, Measurement Condition C)

k) Production of N-(tert-butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide (Reference Example 2)

By the same approach as Reference Example 1-o), from N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide (286 mg), N-(tert-butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide (227 mg) was obtained.

LC-MS: 693 (M+Na)$^+$ (1.658 min, Measurement Condition C)

Reference Example 3

(6S,9S,12S,13E,17R)-9-tert-Butyl-17-{3-[(2,5-di-oxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oic acid tert-butyl ester

[Chemical Formula 23]

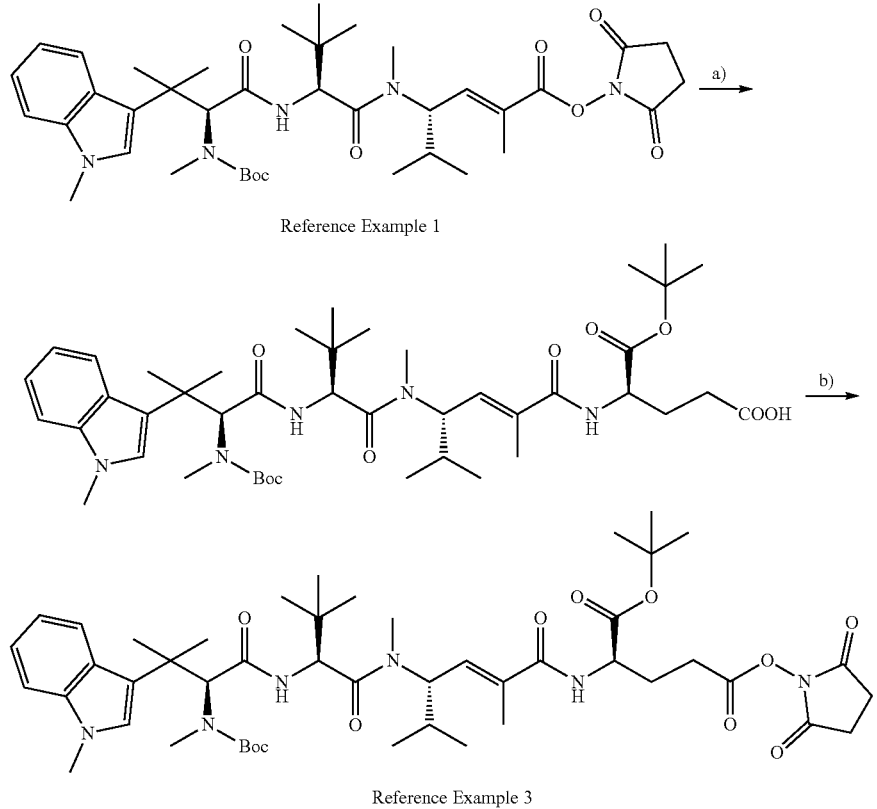

Reference Example 3 a) Production of (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetra oxo-12-(propan-2-yl)-3-oxa-5,8,11,16-tetraazaicos-13-en-20-oic acid A mixed solution of Reference Example 1 (30 mg), D-glutamic acid α-tert-butyl ester hydrochloride (10.7 mg), N,N-diisopropylethylamine (49.7 mg) and N,N-dimethylformamide (1.0 mL) was stirred at 25° C. for 3 hours. After the reaction ended, water was added, and the resultant mixture was extracted with chloroform. The organic layer was washed with water and then dried over anhydrous sodium sulfate, and the solvent was distilled off under reduced pressure. The residue was purified by silica gel column chromatography (eluting solvent; chloroform: methanol) to give (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetra oxo-12-(propan-2-yl)-3-oxa-5,8,11,16-tetraazaicos-13-en-20-oic acid (14.2 mg).

LC-MS: 834 (M+Na)⁺ (1.574 min, Measurement Condition E)

b) Production of (6S,9S,12S,13E,17R)-9-tert-butyl-17-{3-[(2,5-dioxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oic acid tert-butyl ester (Reference Example 3)

By the same approach as Reference Example 1-o), from (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetra oxo-12-(propan-2-yl)-3-oxa-5,8,11,16-tetraazaicos-13-en-20-oic acid (90.2 mg), (6S,9S,12S,13E,17R)-9-tert-butyl-17-{3-[(2,5-dioxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oic acid tert-butyl ester (51.8 mg) was obtained.

LC-MS: 931 (M+Na)⁺ (1.662 min, Measurement Condition E)

Reference Example 4 to 19

The compounds shown in the following table were obtained through the same reaction and treatment as step a) of Reference Example 3, using Reference Example 1 and Reference Example 2 as raw material compounds.

TABLE 1

| Reference Example | Structural Formula | LC-MS/Rt (min) | LC-MS Measurement Condition |
|---|---|---|---|
| 4 | | 745(M + H)+/1.594 | D |
| 5 | | 745(M + H)+/1.526 | D |
| 6 | | 759(M + H)+/1.693 | D |
| 7 | | 759(M + H)+/1.732 | D |

TABLE 1-continued

| Reference Example | Structural Formula | LC-MS/Rt (min) | LC-MS Measurement Condition |
|---|---|---|---|
| 8 | | 745(M + H)+/1.439 | D |
| 9 | | 745(M + H)+/1.400 | D |
| 10 | | 759(M + H)+/1.413 | D |
| 11 | | 759(M + H)+/1.475 | D |
| 12 | | 812(M + H)+/1.560 | D |

TABLE 1-continued
| Reference Example | Structural Formula | LC-MS/Rt (min) | LC-MS Measurement Condition |
|---|---|---|---|
| 13 | 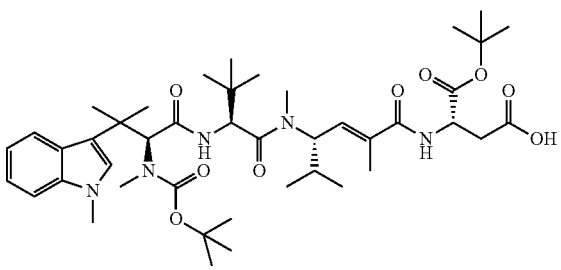 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@@H](CC(=O)O)C(=O)OC(C)(C)C] | 798(M + H)⁺/1.415 | D |
| 14 | 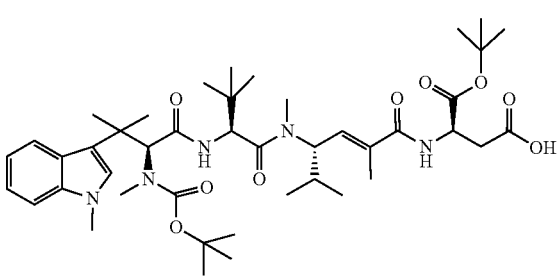 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@H](CC(=O)O)C(=O)OC(C)(C)C] | 798(M + H)⁺/1.474 | D |
| 15 | 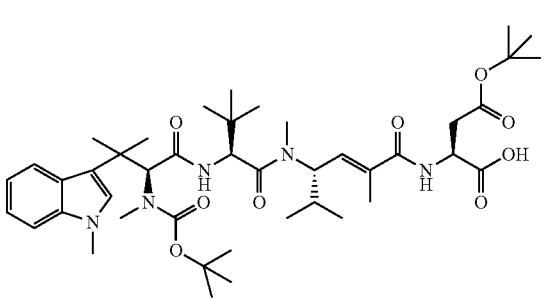 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@@H](CC(=O)OC(C)(C)C)C(=O)O] | 798(M + H)⁺/1.470 | D |
| 16 | 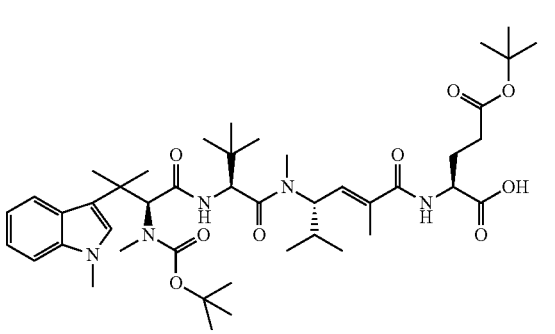 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@@H](CCC(=O)OC(C)(C)C)C(=O)O] | 812(M + H)⁺/1.460 | D |
| 17 | 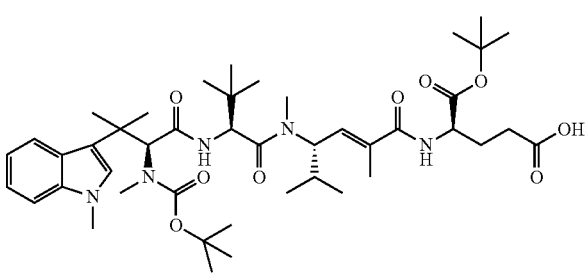 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@H](CCC(=O)O)C(=O)OC(C)(C)C] | 812(M + H)⁺/1.450 | D |

TABLE 1-continued

| Reference Example | Structural Formula | LC-MS/Rt (min) | LC-MS Measurement Condition |
|---|---|---|---|
| 18 | | 798(M + H)⁺/1.420 | D |
| 19 | | 812(M + H)⁺/1.457 | D |

Reference Example 20

The compound shown in the following table was obtained through the same reaction and treatment as step b) of Reference Example 3, using Reference Example 11 as a raw material compound.

TABLE 2

| Reference Example | Structural Formula | LC-MS/Rt (min) | LC-MS Measurement Condition |
|---|---|---|---|
| 20 | | 878 (M + Na)⁺/1.688 | D |

Reference Examples 21 to 23

The compound shown in the following table was obtained through the same reaction and treatment as Reference Example 20.

TABLE 3

| Reference Example | Structural Formula | LC-MS/Rt (min) | LC-MS Measurement Condition |
|---|---|---|---|
| 21 | | 931 (M + Na)⁺/ 1.768 | D |
| 22 | | 895 (M + H)⁺/ 1.512 | D |
| 23 | | 931 (M + Na)⁺/ 2.166 | H |
| 24 | | 895 (M + H)⁺/ 1.850 | H |

Reference Example 25

The compound shown in the following table was obtained through the same reaction and treatment as step o) of Reference Example 1, using taltobulin as a raw material compound.

TABLE 4

| Reference Example | Structural Formula | LC-MS/Rt (min) | LC-MS Measurement Condition |
|---|---|---|---|
| 25 | | 751 (M + H)$^+$/ 1.082 | D |

Reference Examples 26 to 29

The compounds shown in the following table were obtained through the same reaction and treatment as step a) of Reference Example 3, using Reference Example 25 as a raw material compound.

TABLE 5

| Reference Example | Structural Formula | LC-MS/Rt (min) | LC-MS Measurement Condition |
|---|---|---|---|
| 26 | | 645 (M + H)$^+$/ 1.269 | D |
| 27 | | 659 (M + H)$^+$/ 1.265 | D |
| 28 | | 645 (M + H)$^+$/ 1.282 | D |
| 29 | | 659 (M + H)$^+$/ 1.101 | D |

Reference Examples 30 to 32

The compounds shown in the following table were obtained through the same reaction and treatment as step b) of Reference Example 3, using Reference Example 26, Reference Example 27 and Reference Example 28 as raw material compounds.

TABLE 6

| Reference Example | Structural Formula | LC-MS/Rt (min) | LC-MS Measurement Condition |
|---|---|---|---|
| 30 | | 742 (M + H)⁺/ 1.360 | D |
| 31 | | 756 (M + H)⁺/ 1.353 | D |
| 32 | | 742 (M + H)⁺/ 1.013 | D |

Reference Example 33

[Chemical Formula 24]

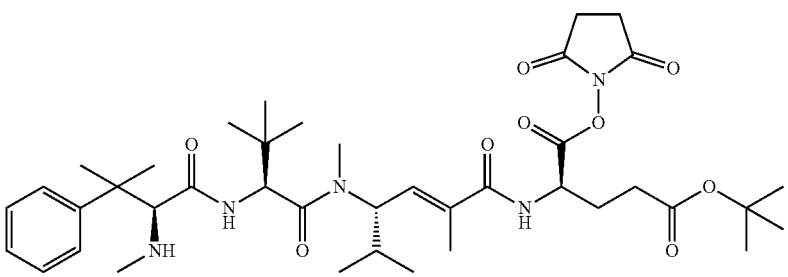

Production of (3S,6S,9S,10E,14R)-6-tert-butyl-14-{[(2,5-dioxopyrrolidin-1-yl)oxy]car bonyl}-8,11-dimethyl-4,7,12-trioxo-3-(2-phenylpropan-2-yl)-9-(propan-2-yl)-2,5,8,13-tetraazaheptadec-10-en-17-oic acid tert-butyl ester Reference Example 33

A mixed solution of Reference Example 28 (173 mg), N-hydroxysuccinimide (30.2 mg), 1-(3-dimethylaminopropyl)-3-ethylcarbodiimide (50.3 mg), tetrahydrofuran (5 mL) and acetonitrile (5 mL) was stirred at 25° C. for 3 days. After the reaction ended, the solvent was distilled off under reduced pressure, and the residue was then purified by silica gel column chromatography (eluting solvent; hexane:ethyl acetate) to give (3S,6S,9S,10E,14R)-6-tert-butyl-14-{[(2,5-dioxopyrrolidin-1-yl)oxy]car bonyl}-8,11-dimethyl-4,7,12-trioxo-3-(2-phenylpropan-2-yl)-9-(propan-2-yl)-2,5,8,13-tetraazaheptadec-10-en-17-oic acid tert-butyl ester (86.9 mg).

LC-MS: 756 (M+H)⁺ (0.348 min, Measurement Condition H)

Example 1

(3S,6S,9S,10E,14R)-6-tert-Butyl-14-{3-[(2,5-di-oxopyrrolidin-1-yl)oxy]-3-oxopropyl}-8,11-dimethyl-4,7,12-trioxo-3-{2-phenylpropan-2-yl)-9-(propan-2-yl)-2,5,8,13-tetraazapentadec-10-en-15-oic acid

[Chemical Formula 25]

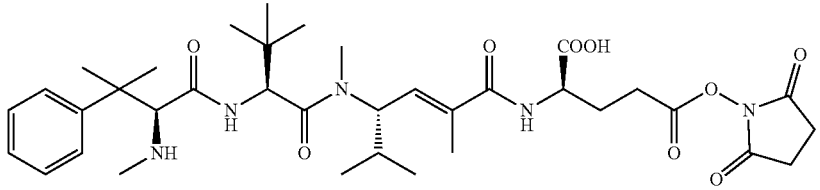

To a solution of Reference Example 20 (24.9 mg) in chloroform (1.0 mL), trifluoroacetic acid (0.2 mL) was added, and the resultant mixture was stirred at 25° C. for 72 hours. After the reaction ended, the reaction solution was concentrated under reduced pressure to give Example 1 (15.6 mg) as a trifluoroacetate.

LC-MS: 700 (M+H)$^+$ (1.140 min, Measurement Condition D)

Examples 2 to 8

The compounds shown in the following table were obtained through the same reaction and treatment as Reference Example 1.

TABLE 7

| Example | Structural Formula | LC-MS/Rt (min) | LC-MS Measurement Condition |
|---|---|---|---|
| 2 | | 686(M + H)$^+$/ 0.150 | G |
| 3 | | 700(M + H)$^+$/ 0.214 | G |
| 4 | | 753(M + H)$^+$/ 0.114 | G |
| 5 | | 686(M + H)$^+$/ 0.111 | G |
| 6 | | 739(M + H)$^+$/ 0.203 | G |

TABLE 7-continued

| Example | Structural Formula | LC-MS/Rt (min) | LC-MS Measurement Condition |
|---|---|---|---|
| 7 | | 753(M + H)+/ 0.110 | G |
| 8 | | 739(M + H)+/ 0.161 | G |

Brentuximab used for Example ADCs in the following is commercially available, or may be produced in accordance with Japanese Patent No. 4303964.

Example ADCT1

Brentuximab-Example 1 conjugate (average DAR: 1.1)

[Chemcial Formula 26]

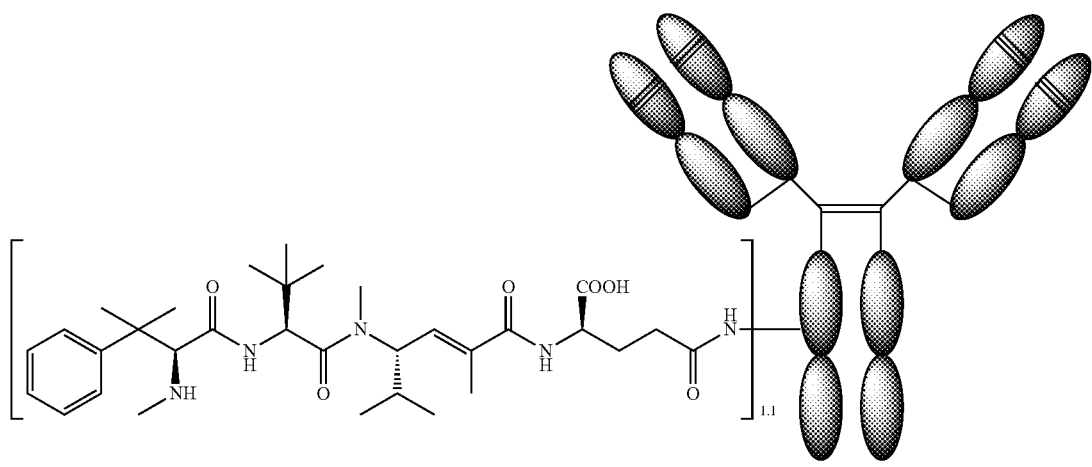

Example ADC1

To a phosphate buffered saline solution (19.5 μL, pH 7.4) of brentuximab (500 μg), a mixed buffer solution (7.17 μL, pH 8.0) of 50 mmol/L potassium phosphate, 50 mmol/L HEPES and 2 mmol/L EDTA and DMSO (5 μL) were added, a 10 mmol/L DMSO solution of Example 1 (13.3 μL) was then added as a modifying agent and completely mixed, and the resultant mixture was incubated at 25° C. for 4 hours. Thereafter, through purification by a PD-10 desalination column pre-equilibrated with a phosphate buffered saline solution (pH 7.4) and subsequent centrifugal concentration, Example ADC1 (257 μg) was obtained.

The average DAR of the ADC thus obtained was measured by LC-MS. Alternatively, the average DAR may be measured qualitatively or quantitatively by ultraviolet-visible absorption spectroscopy (UV-Vis), reducing or non-reducing SDS-PAGE, HPLC-HIC, SEC, RP-HPLC, LC-MS or the like. These methods are described in Antibody Drug Conjugates, Methods in Molecular Biology vol. 1045, 2013. pp 267-284. L. Ducry, Ed.

The average DAR of Example ADC1, determined from LC-MS analysis (Measurement Condition F), was 1.1.

Example ADC2

Brentuximab-Example 1 conjugate (average DAR: 3.5)

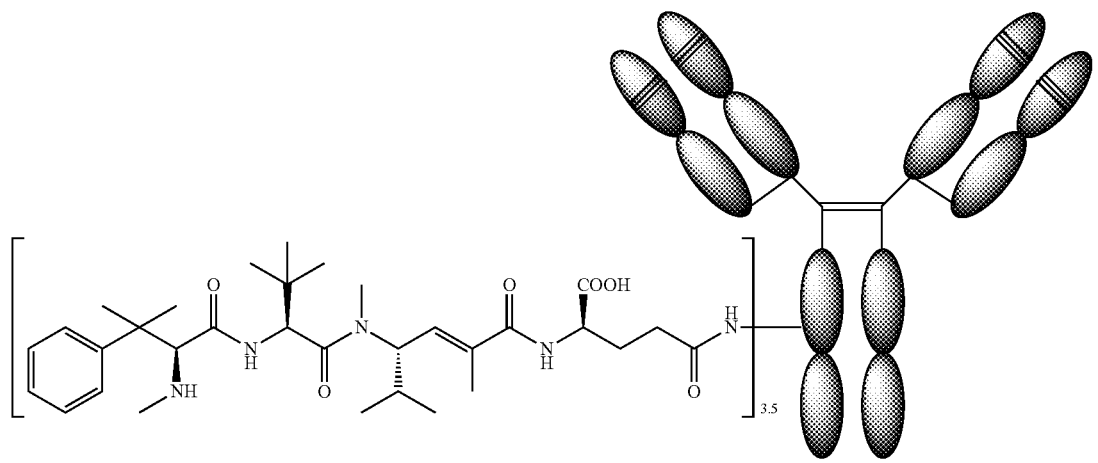

Example ADC2

After adding a mixed buffer solution (45 μL, pH 6.5) of brentuximab (500 μg) in 50 mmol/L potassium phosphate, 50 mmol/L NaCl and 2 mmol/L EDTA and DMSO (5 μL), a 10 mmol/L DMSO solution of Example 1 (13.3 μL) was added as a modifying agent and completely mixed, and the resultant mixture was incubated at 25° C. for 14 hours. Thereafter, through purification by a PD-10 desalination column pre-equilibrated with a phosphate buffered saline solution (pH 7.4) and subsequent centrifugal concentration and analysis of the average DAR under Measurement Condition F, Example ADC2 (285 μg) was obtained.

Example ADC3

Brentuximab-Example 7 conjugate (average DAR: 1.2)

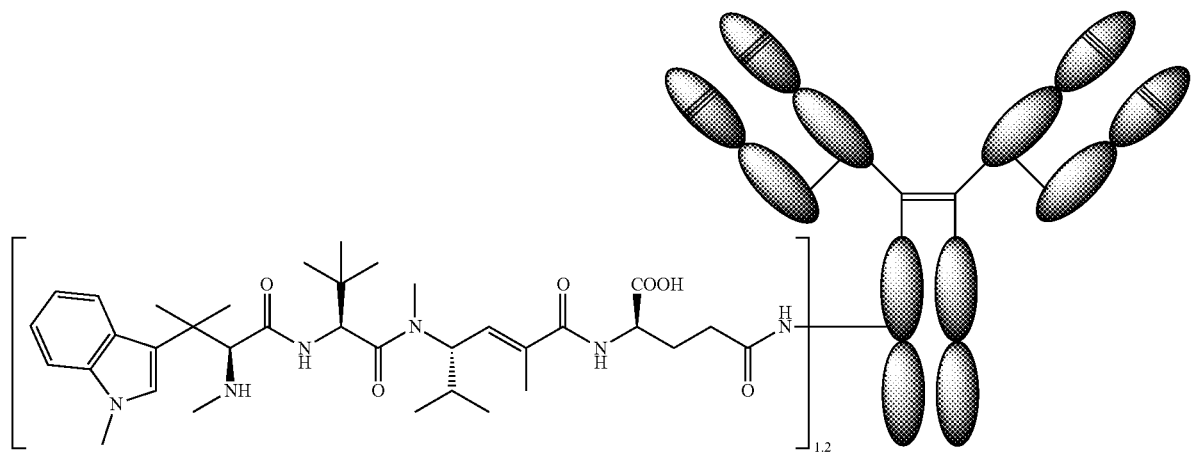

Example ADC3

After adding a mixed buffer solution (45 µL, pH 6.5) of brentuximab (450 µg) in 50 mmol/L potassium phosphate, 50 mmol/L NaCl and 2 mmol/L EDTA and DMSO (5 µL), a 10 mmol/L DMSO solution of Example 7 (6 µL) was added as a modifying agent and completely mixed, and the resultant mixture was incubated at 25° C. for 14 hours. Thereafter, through purification by a PD-10 desalination column pre-equilibrated with a phosphate buffered saline solution (pH 7.4) and subsequent centrifugal concentration and analysis of the average DAR under Measurement Condition F, Example ADC3 (305 µg) was obtained.

Examples ADC4 to 9

The ADCs shown in the following table were obtained through the same reaction and treatment as Example ADC2, using corresponding antibodies and modifying agents (compounds of Examples).

TABLE 8

| Example | Antibody | Modifying agent | Average DAR | Measurement condition |
|---|---|---|---|---|
| ADC4 | Brentuximab | Example 2 | 0.46 | F |
| ADC5 | Brentuximab | Example 3 | 1.51 | F |
| ADC6 | Brentuximab | Example 4 | 2.93 | F |
| ADC7 | Brentuximab | Example 6 | 1.64 | F |
| ADC8 | Brentuximab | Example 8 | 1.17 | F |

Examples ADC9 to 12

The ADCs shown in the following table were obtained through the same reaction and treatment as Example ADC3, using corresponding antibodies and modifying agents (compounds of Examples).

TABLE 9

| Example | Antibody | Modifying agent | Average DAR | Measurement condition |
|---|---|---|---|---|
| ADC9 | Gemtuzumab | Example 1 | 3.49 | F |
| ADC10 | Gemtuzumab | Example 7 | 1.77 | F |
| ADC11 | Inotuzumab | Example 1 | 3.98 | F |
| ADC12 | Trastuzumab | Example 1 | 3.95 | F |

Hereinafter, results of pharmacological tests with respect to particular Examples of the antibody-drug conjugate according to the present invention will be shown and its pharmacological actions will be explained, but the present invention is not limited to these Test Examples.

Test Example 1: Cellular Toxicity Test (1)

Karpas-299 cells (European Collection of Authenticated Cell Cultures, hereinafter, ECACC), which are CD30 antigen-expressing cell lines and human lymphoma cell lines, were cultured in RPMI 1640 (GIBCO) containing 10% fetal bovine serum (MP Biomedicals) (hereinafter, referred to as "culture medium A" in this test). Karpas-299 cells were prepared to be $2 \times 10^6$ cells/mL in culture medium A, and were added to a 96 well microplate for cell culturing in an amount of 50 µL for each well. Brentuximab, Example ADC1 or Example ADC2 prepared to be in a concentration of 16 µg/mL with culture medium A was added to the microplate in an amount of 50 µL for each well, and culture was carried out at 37° C. under 5% $CO_2$ for 4 days. After culturing, the microplate was taken out from the incubator, and was left at rest at room temperature for 10 minutes. To each well, 50 µL of CellTiter-Glo Luminescent Cell Viability Assay (Promega) was added, and the resultant mixture was stirred. This mixture was incubated at a dark place for 20 minutes, and luminescence was measured by using a microplate luminometer, thereby determining the percentage of the number of cells remaining after treatment with brentuximab, Example ADC1 or Example ADC2 to the number of cells remaining after treatment with addition of no compound. The results are shown in the following Table 10.

TABLE 10

| Cell | Compound | Cell remaining rate (%) |
|---|---|---|
| Karpas-299 | Without addition | 100 |
| | Brentuximab | 71.5 |
| | Example ADC1 | 42.6 |
| | Example ADC2 | 15.2 |

As shown in Test Example 1, when Example ADCs were used, more remarkable reduction in the number of cells was confirmed than when brentuximab, which is their antibody moiety, was used. From this, it was revealed that the ADCs according to the present invention exhibit stronger cellular toxicities DAR-dependently, compared to the antibody without being conjugated with a drug.

From the results of Test Example 1, it was found that the compounds of Examples represented by formula (1) exhibit stronger activities in the cellular toxicity test than the antibody by conjugating with a lysine residue of the antibody to form the conjugate represented by formula (2).

Test Example 2: Cellular Toxicity Test (2)

Karpas-299 cells (European Collection of Authenticated Cell Cultures, hereinafter, ECACC), which are CD30 antigen-expressing cell lines and human lymphoma cell lines, were cultured in RPMI 1640 (GIBCO) containing 10% fetal bovine serum (MP Biomedicals) (hereinafter, referred to as "culture medium A" in this test). Karpas-299 cells were prepared to be $2 \times 10^6$ cells/mL in culture medium A, and were added to a 96 well microplate for cell culturing in an amount of 50 µL for each well. Each compounds prepared to be in a concentration of 0.25 µM with culture medium A was added to the microplate in an amount of 50 µL for each well, and culture was carried out at 37° C. under 5% $CO_2$ for 4 days. After culturing, the microplate was taken out from the incubator, and was left at rest at room temperature for 10 minutes. To each well, 50 µL of CellTiter-Glo Luminescent Cell Viability Assay (Promega) was added, and the resultant mixture was stirred. This mixture was incubated at a dark place for 20 minutes, and luminescence was measured by using a microplate luminometer, thereby determining the percentage of the number of cells remaining after treatment with each compound to the number of cells remaining after treatment with addition of no compound. The results are shown in the following Table 11.

TABLE 11

| Cell | Compound | Cell remaining rate (%) |
|---|---|---|
| Karpas-299 | Without addition | 100 |
|  | Comparative Example compound | 18.1 |
|  | Metabolite of Example ADC1 | 100 |

Comparative Example compound in the above Table 11 represents the following compound formed after an antibody-drug conjugate synthesized from a compound disclosed in International Publication No. WO 2014/057436 is metabolized under the mechanism described in Non Patent Literature 7 in target cells.

[Chemical Formula 29]

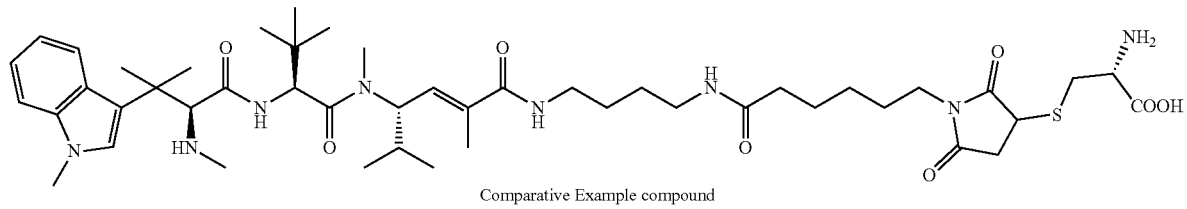

Comparative Example compound

The metabolite of Example ADC1 in the above Table 11 represents the following compound formed after Example ADC1 is metabolized under the mechanism described in Non Patent Literature 8 in target cells.

[Chemical Formula 30]

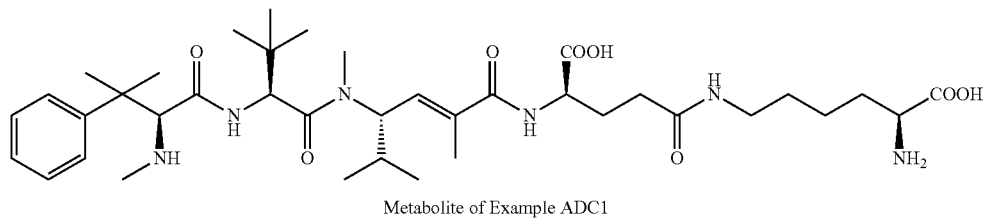

Metabolite of Example ADC1

As shown in Test Example 2, it was shown that in contrast to Comparative Example compound, which exhibited strong cellular toxicity, the metabolite of Example ADC1 exhibits weak cytotoxic activity.

Test Example 3: Evaluation of Activity for Inhibiting Microtubule Polymerization Using Porcine Tubulins Using a tubulin polymerization inhibition assay kit (catalog number: BK006P) purchased from Cytoskeleton Inc., the polymerization inhibitory activity of compounds of Examples was evaluated in accordance with the protocol appended to the kit. To a 96 well microplate, 80 mM PIPES pH 6.9, 2 mM MgCl, 0.5 mM EGTA and 5% DMSO buffered solution of the compound to be evaluated was added in an amount of 10 μL for each well, and to these wells, 3 mg/mL porcine tubulin 80 mM PIPES pH 6.9, 2 mM MgCl, 0.5 mM EGTA, 1 mM GTP and 10.2% glycerol solution was added in an amount of 100 μL for each well. In order to examine a state in which tubulins polymerize over time, the absorbance at 340 nm was measured at 37° C., using a microplate reader. As the polymerization of tubulins progresses, the absorbance at 340 nm rises.

The tubulin polymerization inhibitory activity was evaluated based on the proportion of polymerized tubulins 60 minutes after the assay initiation. Specifically, the microtubule polymerization rate (%) was calculated by dividing the absorbance of tubulins that had polymerized at wells to which the compound had been added by the absorbance of tubulins that had polymerized at wells to which the compound had not been added, and multiplying the obtained value by 100. The results are shown in the following Table 12.

TABLE 12

| Compound | Microtubule polymerization rate (%) |
|---|---|
| Comparative Example compound | 0 |
| Metabolite of Example ADC1 | 1.7 |

The above results are those at 9.1 μM.

It is indicated that the lower value the microtubule polymerization rate is, the more strongly the compound inhibits polymerization of microtubules.

As seen from the results of Test Example 3, Comparative Example compound and the metabolite of Example ADC1 exhibit comparable activities for inhibiting microtubule polymerization.

As seen from the results of Test Examples 1 to 3, the ADCs according to the present invention each form a metabolite in antigen-expressing cells to exhibit cellular toxicity. As such, the metabolites formed from the ADCs according to the present invention are expected to cause reduced side effects even if being released out of cells through cell death or the like to cause systemic exposure, because of its weak cellular toxicity.

Test Example 4: Cellular Toxicity Test (3)

Karpas-299 cells (European Collection of Authenticated Cell Cultures, hereinafter, ECACC), which are CD30 antigen-expressing cell lines and human lymphoma cell lines, were cultured in RPMI 1640 (GIBCO) containing 10% fetal bovine serum (MP Biomedicals) (hereinafter, referred to as "culture medium A" in this test).

Karpas-299 cells were prepared to be $2 \times 10^6$ cells/mL in culture medium A, and were added to a 96 well microplate for cell culturing in an amount of 50 µL for each well. Each Example ADC prepared to be in a concentration of 16 µg/mL with culture medium A were added to the microplate in an amount of 50 µL for each well, and culture was carried out at 37° C. under 5% $CO_2$ for 4 days. After culturing, the microplate was taken out from the incubator, and was left at rest at room temperature for 10 minutes. To each well, 50 µL of CellTiter-Glo Luminescent Cell Viability Assay (Promega) was added, and the resultant mixture was stirred. This mixture was incubated at a dark place for 20 minutes, and luminescence was measured by using a microplate luminometer, thereby determining the percentage of the number of cells remaining after treatment with each Example ADC to the number of cells remaining after treatment with addition of no compound. The results are shown in the following Table 13.

TABLE 13

| Cell | Compound | Cell remaining rate (%) |
|---|---|---|
| Karpas-299 | Example ADC3 | 9.9 |
| | Example ADC4 | 46.1 |
| | Example ADC5 | 17.7 |
| | Example ADC6 | 8.3 |
| | Example ADC7 | 17.2 |
| | Example ADC8 | 10.3 |

Test Example 5: Cellular Toxicity Test for ADCs

The activities of ADCs were evaluated in accordance with the method described in Test Example 1 or Test Example 4 to show the results in the following Table 14.

TABLE 14

| Compound | Cell | Cell remaining rate (%) |
|---|---|---|
| Example ADC9 | THP1 | 30.9 |
| Example ADC10 | THP1 | 13.8 |
| Example ADC11 | Ramos | 0.2 |
| Example ADC12 | HCC1954 | 9.6 |

INDUSTRIAL APPLICABILITY

As explained above, the antibody-drug conjugate according to the present invention is expected to be an anticancer agent excellent in safety that exhibits cytotoxic activity selectively to antigen-expressing cells.

The invention claimed is:
1. A compound represented by formula (1):

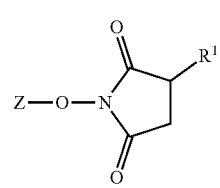

wherein $R^1$ represents a hydrogen atom or a sulfonyl group; and

Z represents a group represented by formula (Z-1), formula (Z-2) or formula (Z-3):

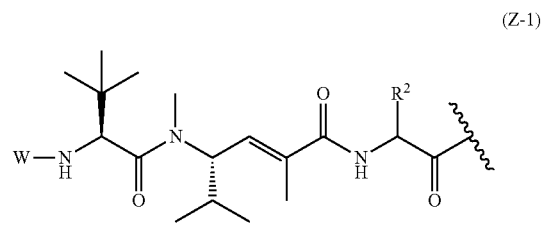

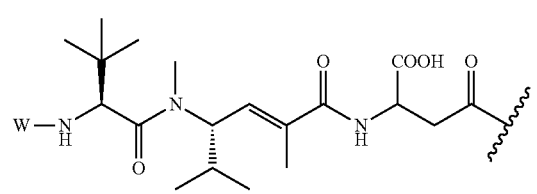

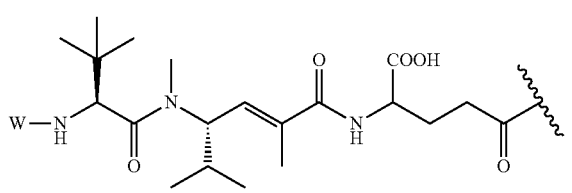

where

W represents a group represented by formula (W-1):

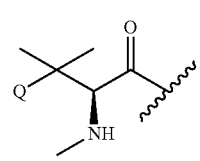

where
  Q represents a group represented by formula (Q-1) or formula (Q-2):

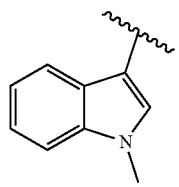
(Q-1)

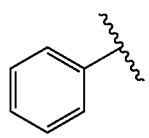
(Q-2)

R² represents —(CH₂)$_u$—COOH; and
u represents 1 or 2,
or a salt thereof.

2. The compound according to claim 1, wherein R¹ is a hydrogen atom, or a salt thereof.

3. The compound according to claim 1, selected from the following compound:

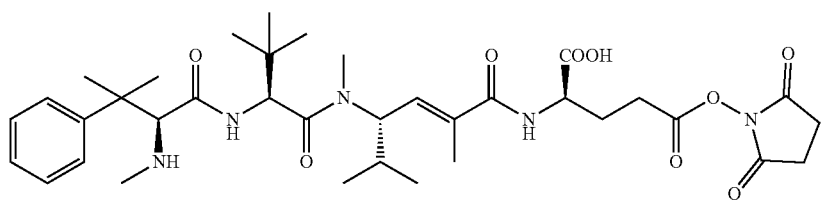 [SMILES: CN[C@H](C(=O)N[C@H](C(=O)N(C)[C@H](/C=C(\C)C(=O)N[C@H](CCC(=O)ON1C(=O)CCC1=O)C(=O)O)C(C)C)C(C)(C)C)C(C)(C)c1ccccc1]

or a salt thereof.

4. An antibody-drug conjugate represented by formula (2):

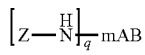
(2)

wherein
  mAb represents an antibody;
  q represents an integer of 1 to 30; and
  Z represents a group represented by formula (Z-1), formula (Z-2) or formula (Z-3):

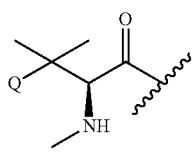
(Z-1)

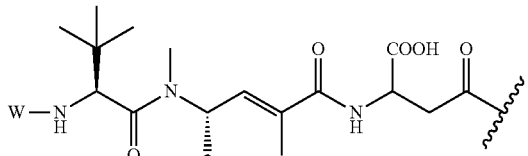
(Z-2)

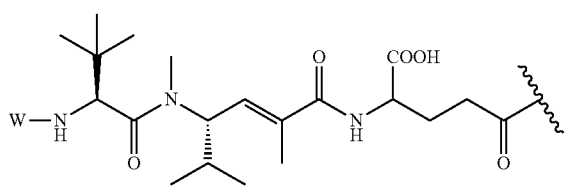
(Z-3)

where
  W represents a group represented by formula (W-1):

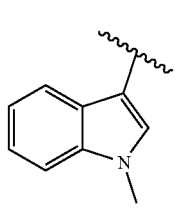
(W-1)

where
  Q represents a group represented by formula (Q-1) or formula (Q-2):

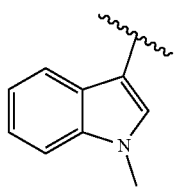
(Q-1)

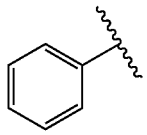
(Q-2)

R² represents —(CH₂)$_u$—COOH; and
u represents 1 or 2,
or a pharmaceutically acceptable salt thereof.

5. The antibody-drug conjugate according to claim 4, wherein mAb is brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, lorvotuzumab, rituximab, depatuxizumab, denintuzumab, enfortumab, telisotuzumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vanticumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab, camidanlumab, cofetuzumab, ladiratuzumab, loncastuximab, telisotuzumab, enapotamab, an antibody of AMG 595 or anti-embigin antibody,
or a pharmaceutically acceptable salt thereof.

6. The antibody-drug conjugate according to claim 4, wherein mAb is brentuximab,
or a pharmaceutically acceptable salt thereof.

7. The antibody-drug conjugate according to claim 4, wherein q is an integer of 1 to 20,
or a pharmaceutically acceptable salt thereof.

8. The antibody-drug conjugate according to claim 4, wherein q is an integer of 1 to 10,
or a pharmaceutically acceptable salt thereof.

9. A pharmaceutical composition comprising the antibody-drug conjugate according to claim 4 or a pharmaceutically acceptable salt thereof.

10. A pharmaceutical composition comprising:
the antibody-drug conjugate according to claim 4 or a pharmaceutically acceptable salt thereof; and
one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof.

11. An anticancer agent comprising the antibody-drug conjugate according to claim 4, or a pharmaceutically acceptable salt thereof.

12. A method of treating cancer, comprising administering the antibody-drug conjugate according to claim 4 or a pharmaceutically acceptable salt thereof to a patient in need thereof.

13. A method of treating cancer, comprising administering the antibody-drug conjugate according to claim 4 or a pharmaceutically acceptable salt thereof and one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof to a patient in need thereof.

14. The method according to claim 12, wherein cancer is breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma or leukemia.

* * * * *